(12) United States Patent
Siegert

(10) Patent No.: US 11,505,481 B2
(45) Date of Patent: Nov. 22, 2022

(54) MULTI-PURPOSE BIO-ELECTRICAL MODULES AND PROCEDURES

(71) Applicant: Michael Siegert, Lausanne (CH)

(72) Inventor: Michael Siegert, Lausanne (CH)

( * ) Notice: Subject to any disclaimer, the term of this patent is extended or adjusted under 35 U.S.C. 154(b) by 523 days.

(21) Appl. No.: 16/607,025

(22) PCT Filed: Apr. 18, 2018

(86) PCT No.: PCT/IB2018/052671
§ 371 (c)(1),
(2) Date: Oct. 21, 2019

(87) PCT Pub. No.: WO2018/193381
PCT Pub. Date: Oct. 25, 2018

(65) Prior Publication Data
US 2020/0131063 A1 Apr. 30, 2020

Related U.S. Application Data

(60) Provisional application No. 62/492,163, filed on Apr. 29, 2017, provisional application No. 62/487,485, filed on Apr. 20, 2017.

(51) Int. Cl.
*C25C 3/20* (2006.01)
*C02F 3/00* (2006.01)
(Continued)

(52) U.S. Cl.
CPC .............. *C02F 3/005* (2013.01); *C02F 1/20* (2013.01); *C02F 1/46109* (2013.01);
(Continued)

(58) Field of Classification Search
CPC ........... C25B 15/02; C25B 15/00; C25B 9/00; C25B 11/00; C25C 7/06; C25C 3/20; C25C 3/16; C25C 7/00
See application file for complete search history.

(56) References Cited

U.S. PATENT DOCUMENTS

| 3,893,897 A | 7/1975 | Raetzsch et al. |
| 6,315,886 B1 | 11/2001 | Zappi et al. |
| 2002/0017467 A1* | 2/2002 | Ando .................. F02D 41/2474 |
| | | 204/426 |

FOREIGN PATENT DOCUMENTS

| CA | 1001114 | 12/1976 |
| CA | 2951389 | 12/2015 |
| JP | 3177849 B2 | 6/2001 |

OTHER PUBLICATIONS

Extended European Search Report for EP18787601.6, dated Feb. 17, 2021.

(Continued)

*Primary Examiner* — Zulmariam Mendez
(74) *Attorney, Agent, or Firm* — Ridout & Maybee LLP

(57) ABSTRACT

The invented bio-electrical system is a housing-electrode which allows insertion of another electrode for various electrochemical and bio-electrical applications. Together with other invented elements as well as standard components, the system is fully scalable, modular, and allows production and collection of gases under pressure. It can be built in many shapes, such as the embodied tubular shape. The design allows operation on unstable ground, for example on ships. Flow of electrolyte can be regulated and directed in cascaded reactions by opening and closing the compartments of the outer or the inner electrodes using the provided electrode holders. The redox conditions inside the system can be controlled using off-the-shelf power supplies which are controlled using the provided algorithm. Gas collection can be regulated based on the level of liquid inside the system using the provided float switches or conductivity probes even as the system is moving or operated under zero-gravity conditions.

6 Claims, 12 Drawing Sheets

(51) Int. Cl.

| | |
|---|---|
| *C02F 1/20* | (2006.01) |
| *C02F 1/461* | (2006.01) |
| *C02F 3/10* | (2006.01) |
| *C02F 3/34* | (2006.01) |
| *C12M 1/04* | (2006.01) |
| *C12M 1/00* | (2006.01) |
| *C12M 1/42* | (2006.01) |
| *C25B 11/02* | (2021.01) |
| *C25B 15/02* | (2021.01) |
| *C25B 3/25* | (2021.01) |
| *C25B 9/17* | (2021.01) |
| *C25B 9/65* | (2021.01) |
| *C25B 9/70* | (2021.01) |

(52) U.S. Cl.
CPC .............. *C02F 3/104* (2013.01); *C02F 3/348* (2013.01); *C12M 23/24* (2013.01); *C12M 23/26* (2013.01); *C12M 35/02* (2013.01); *C25B 3/25* (2021.01); *C25B 9/17* (2021.01); *C25B 9/65* (2021.01); *C25B 9/70* (2021.01); *C25B 11/02* (2013.01); *C25B 15/02* (2013.01); *C02F 2201/003* (2013.01); *C02F 2201/46135* (2013.01); *C02F 2203/006* (2013.01)

(56) References Cited

OTHER PUBLICATIONS

International Search Report and Written Opinion issued in PCT/IB2018/052671 dated Aug. 29, 2018.
Partial Supplementary European Search Report; EP 18787601.6 dated Nov. 17, 2020.
Machine Translation of JP 3177849; Japan Atomic Energy Res Inst Jun. 18, 2001.

\* cited by examiner

Fig 2A
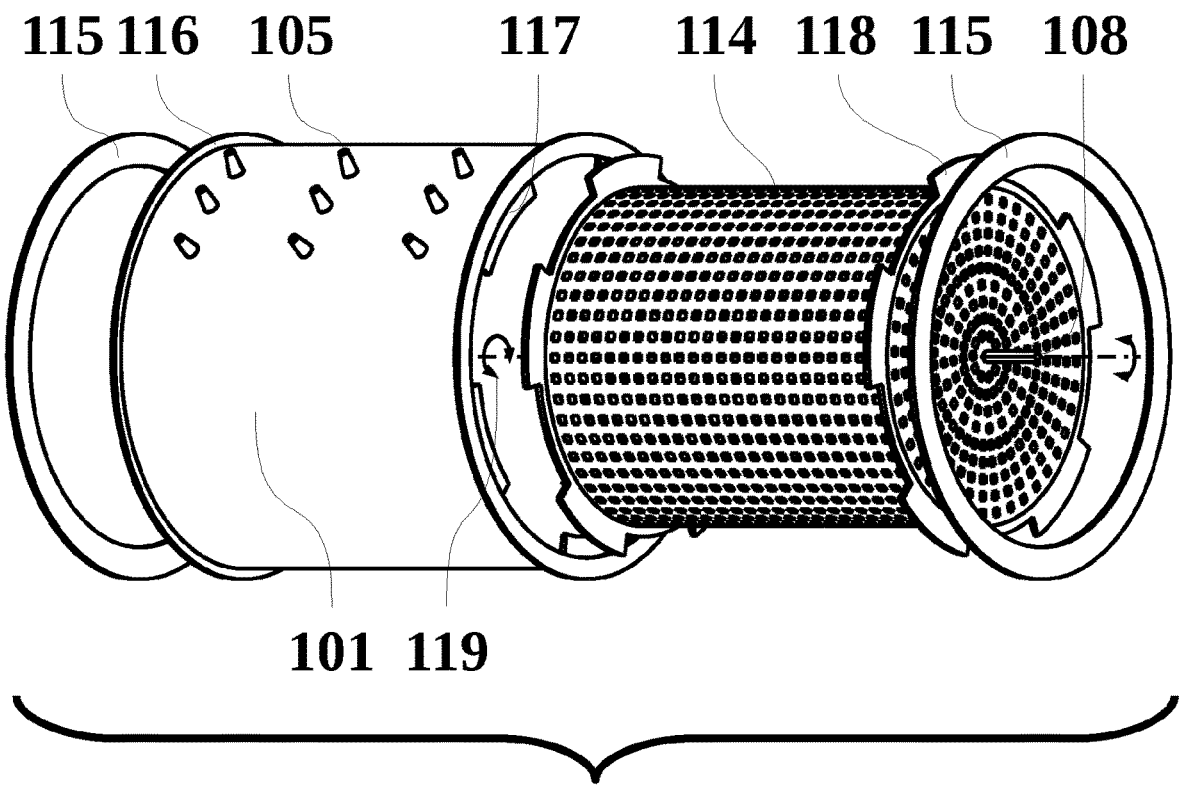
B
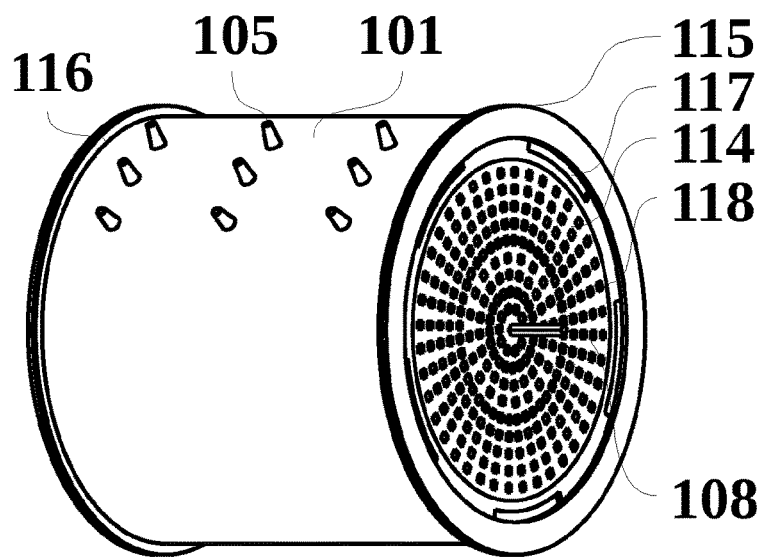

Fig 3A
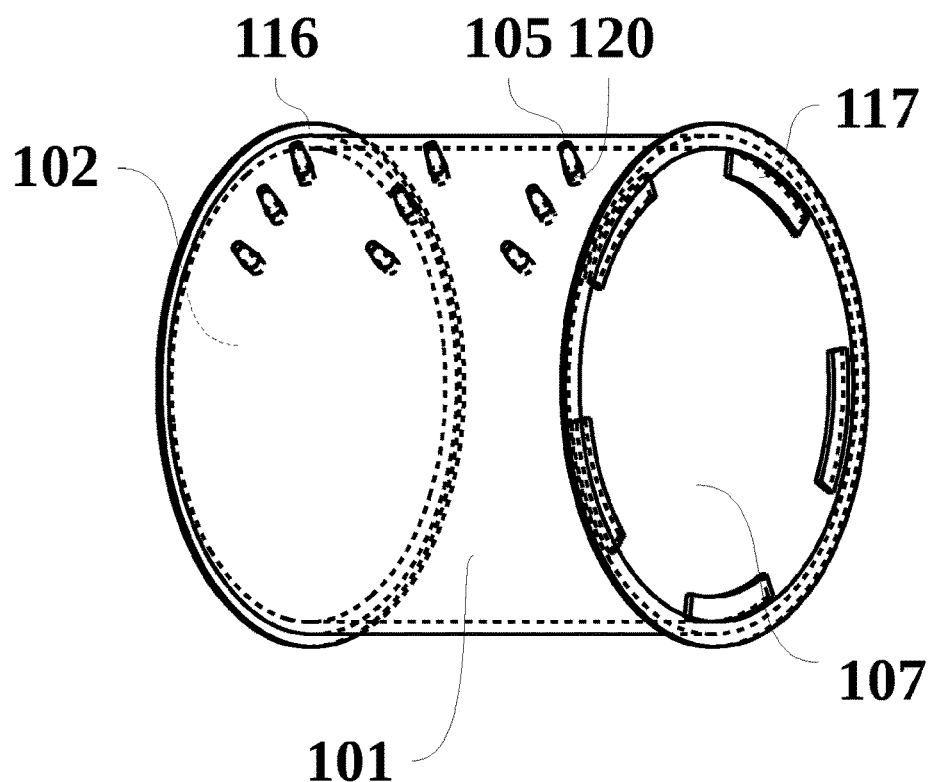
B                                C
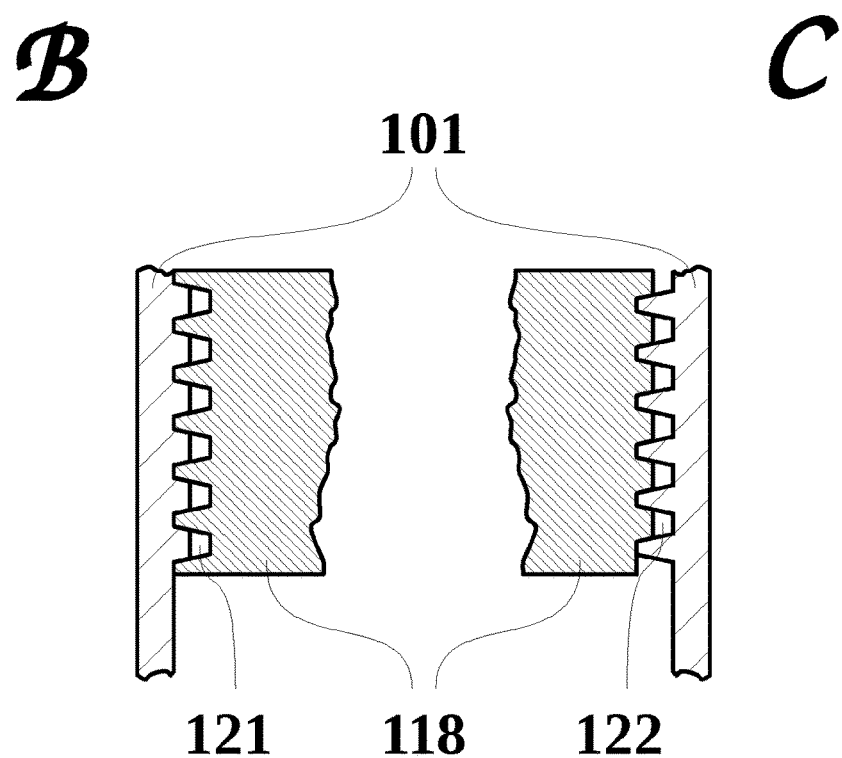

Fig 4A
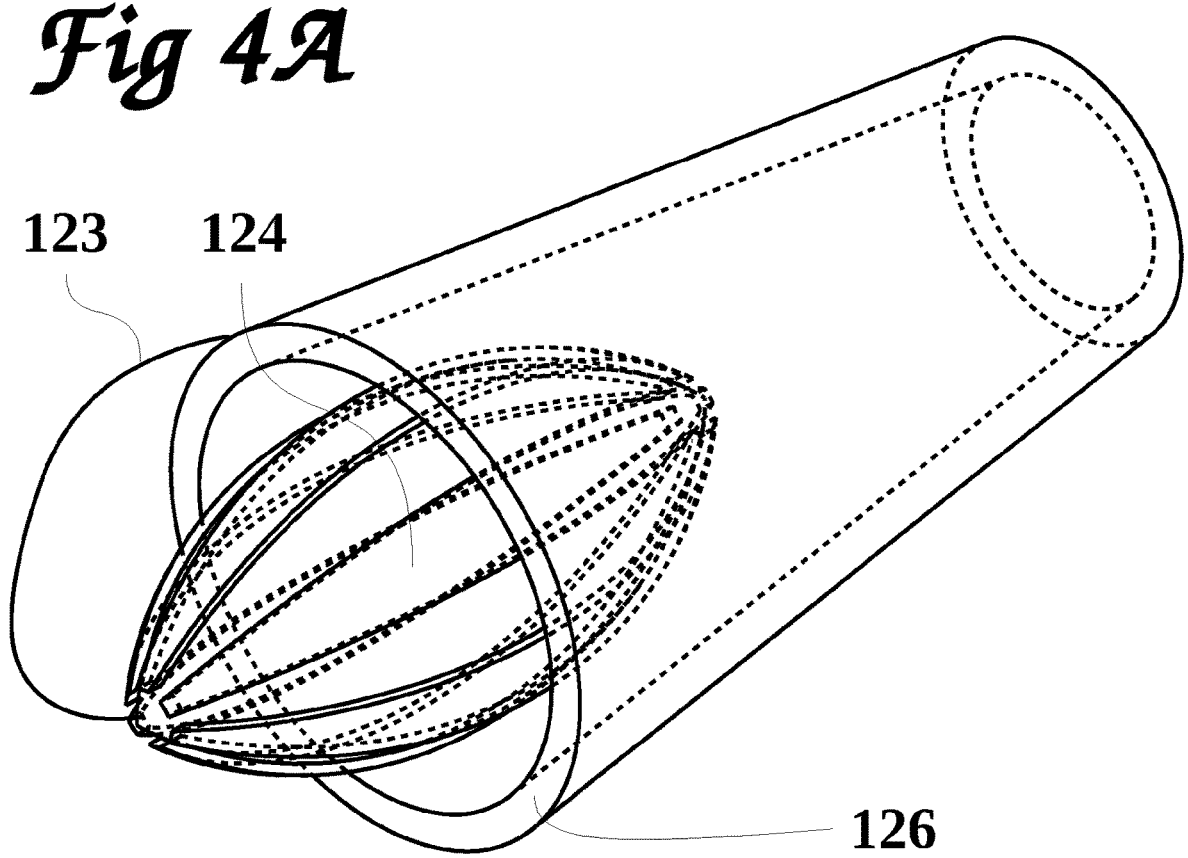
B
Top
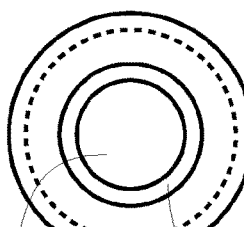
125
Side
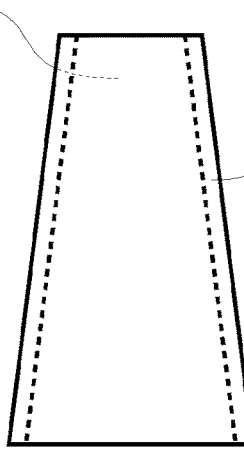
126
C
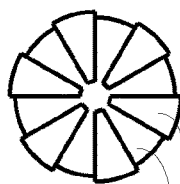
127
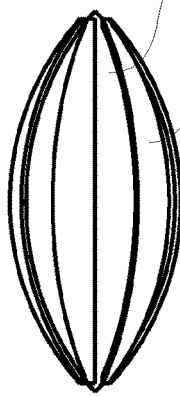
128
D
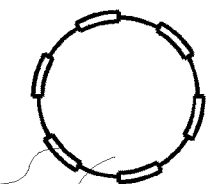
128
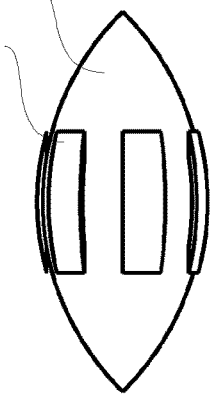

Fig 5A
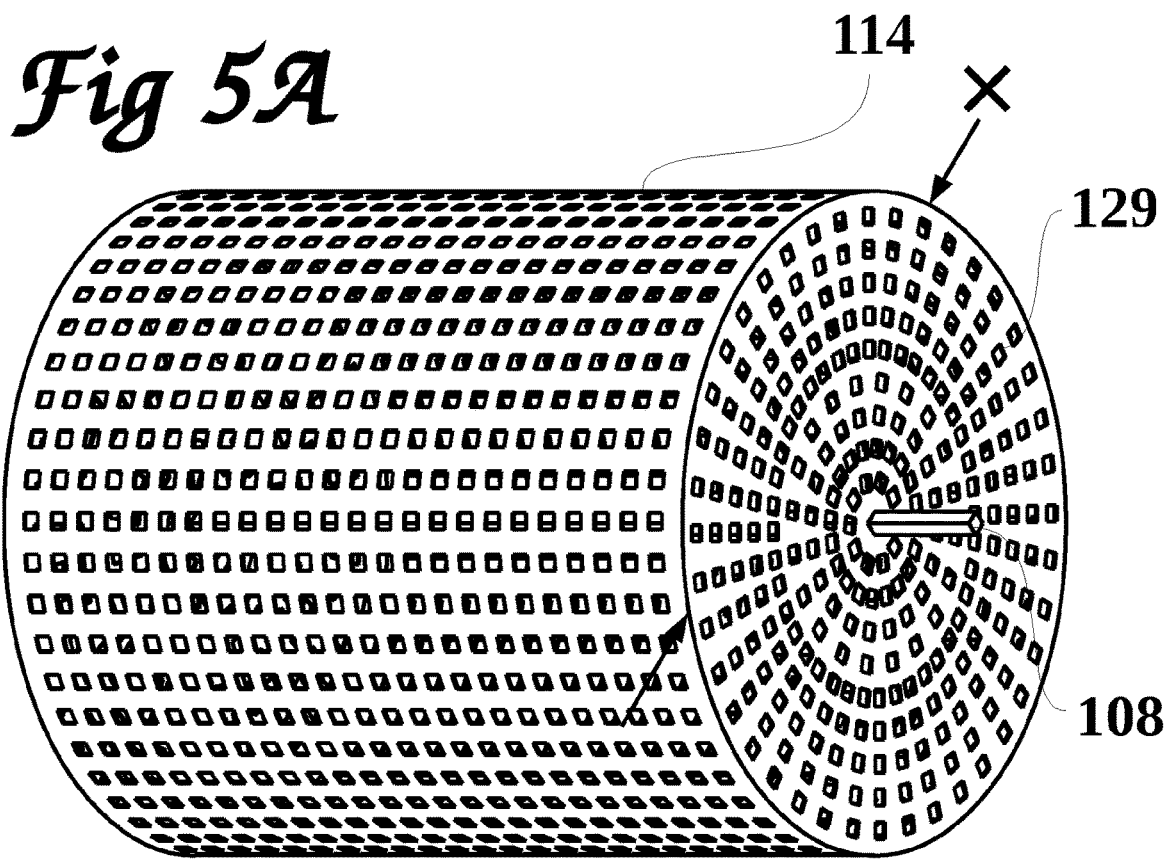
B
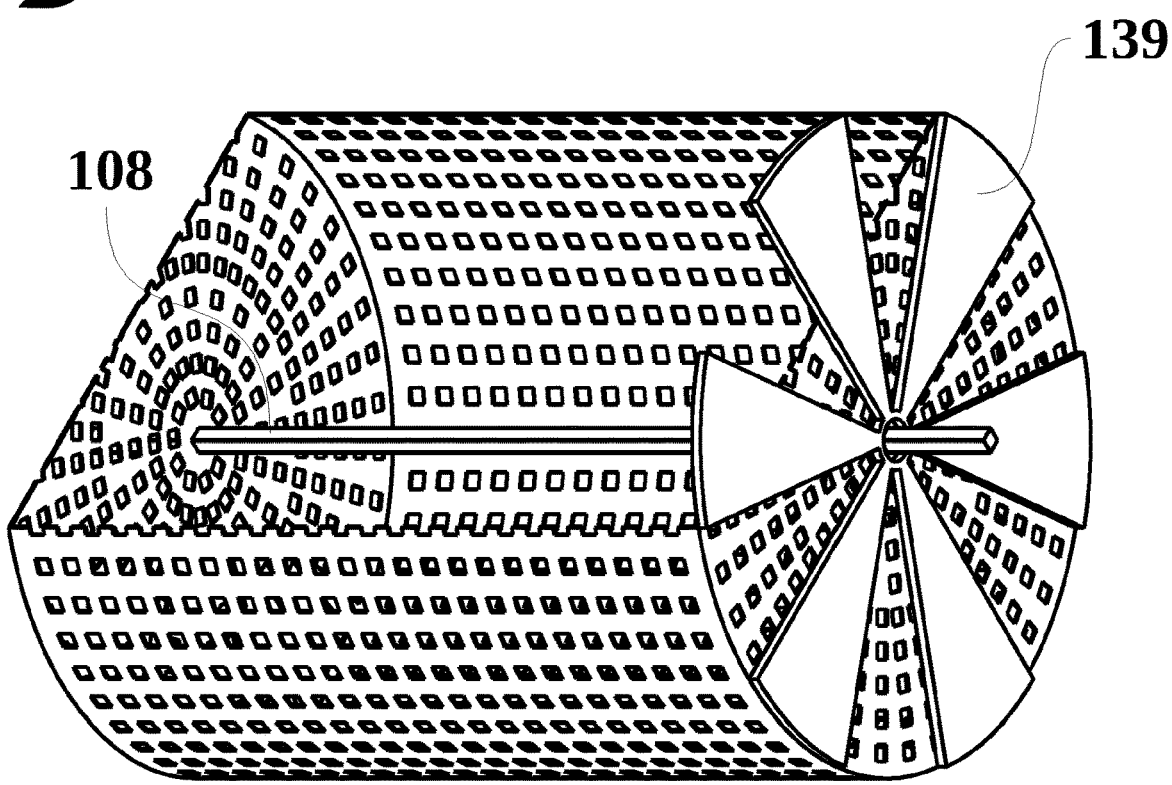

Fig 6A
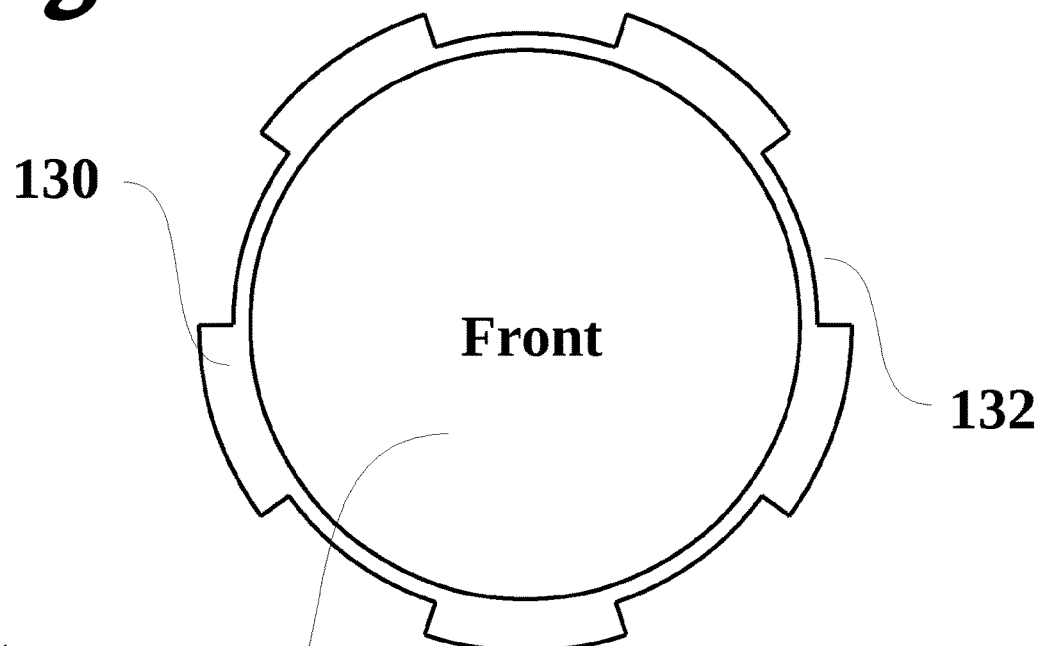
B
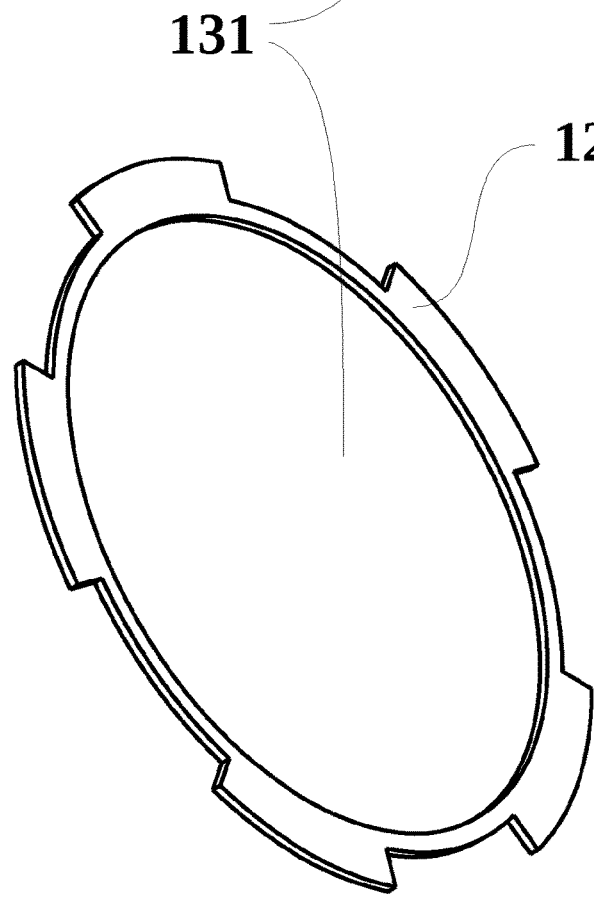
C
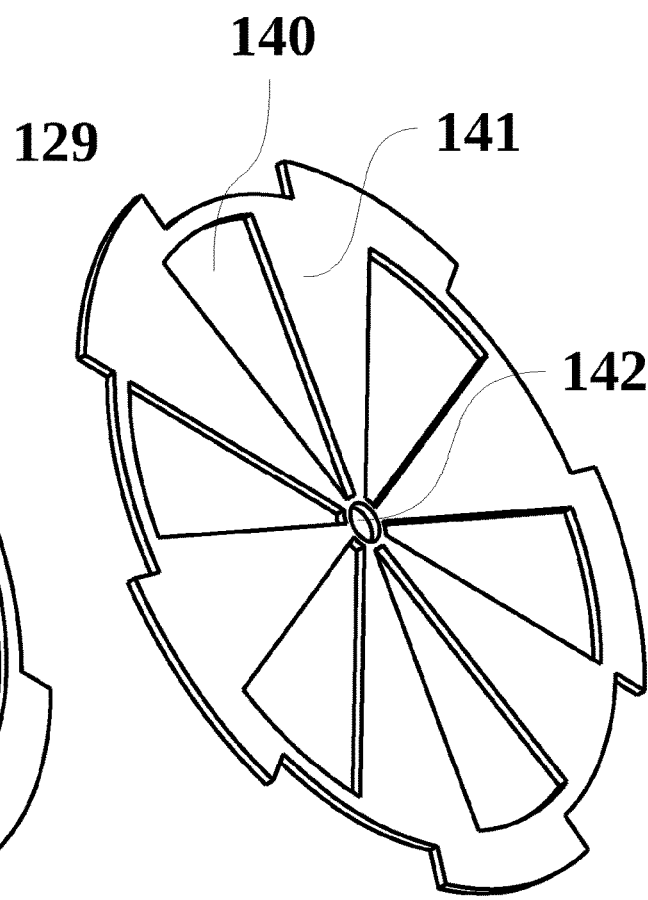

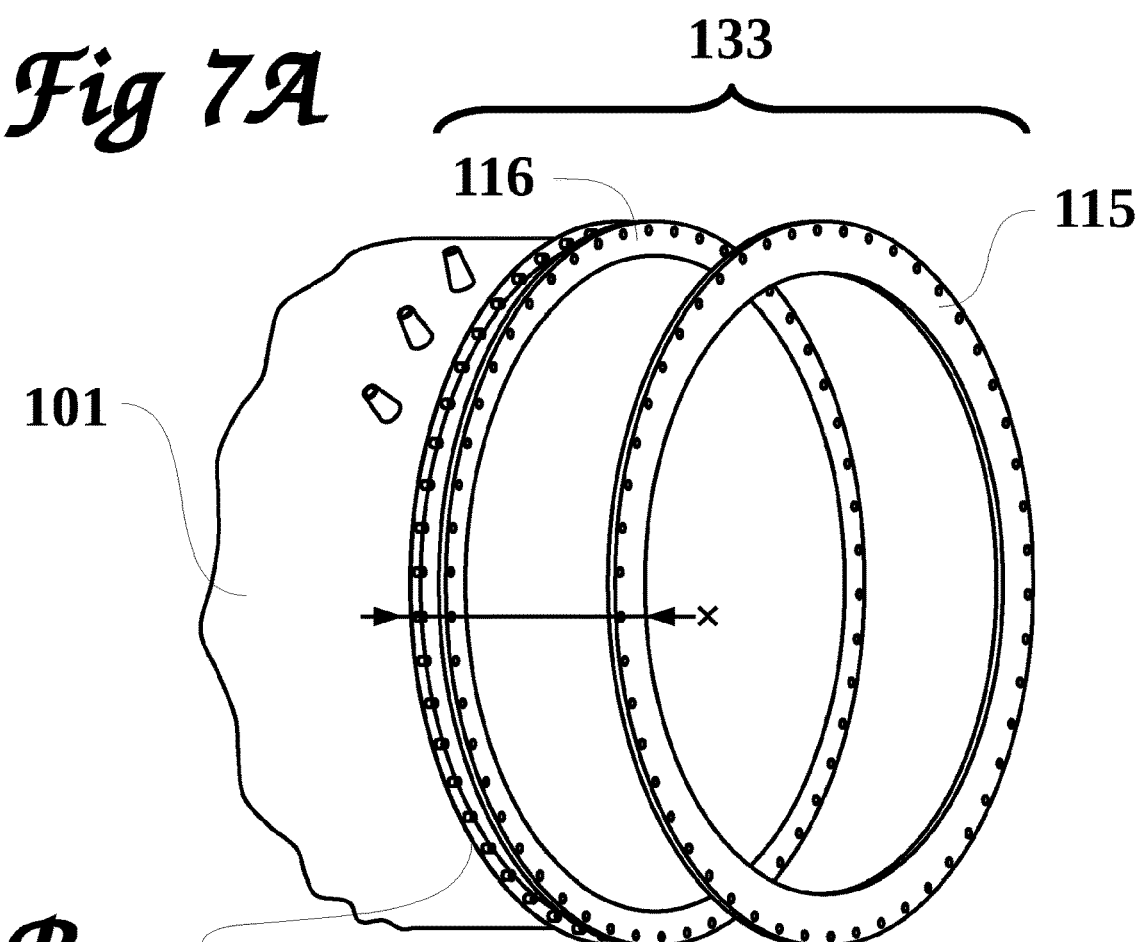
*Fig 7A*
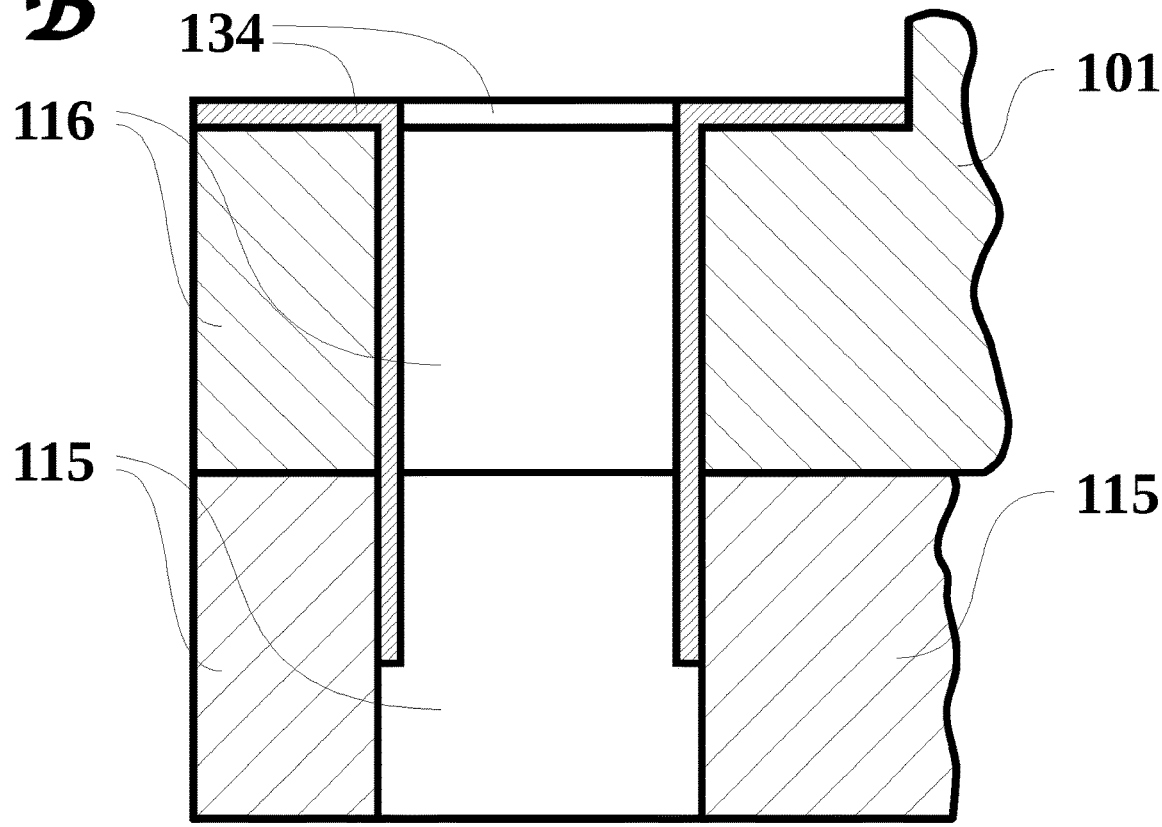
*B*

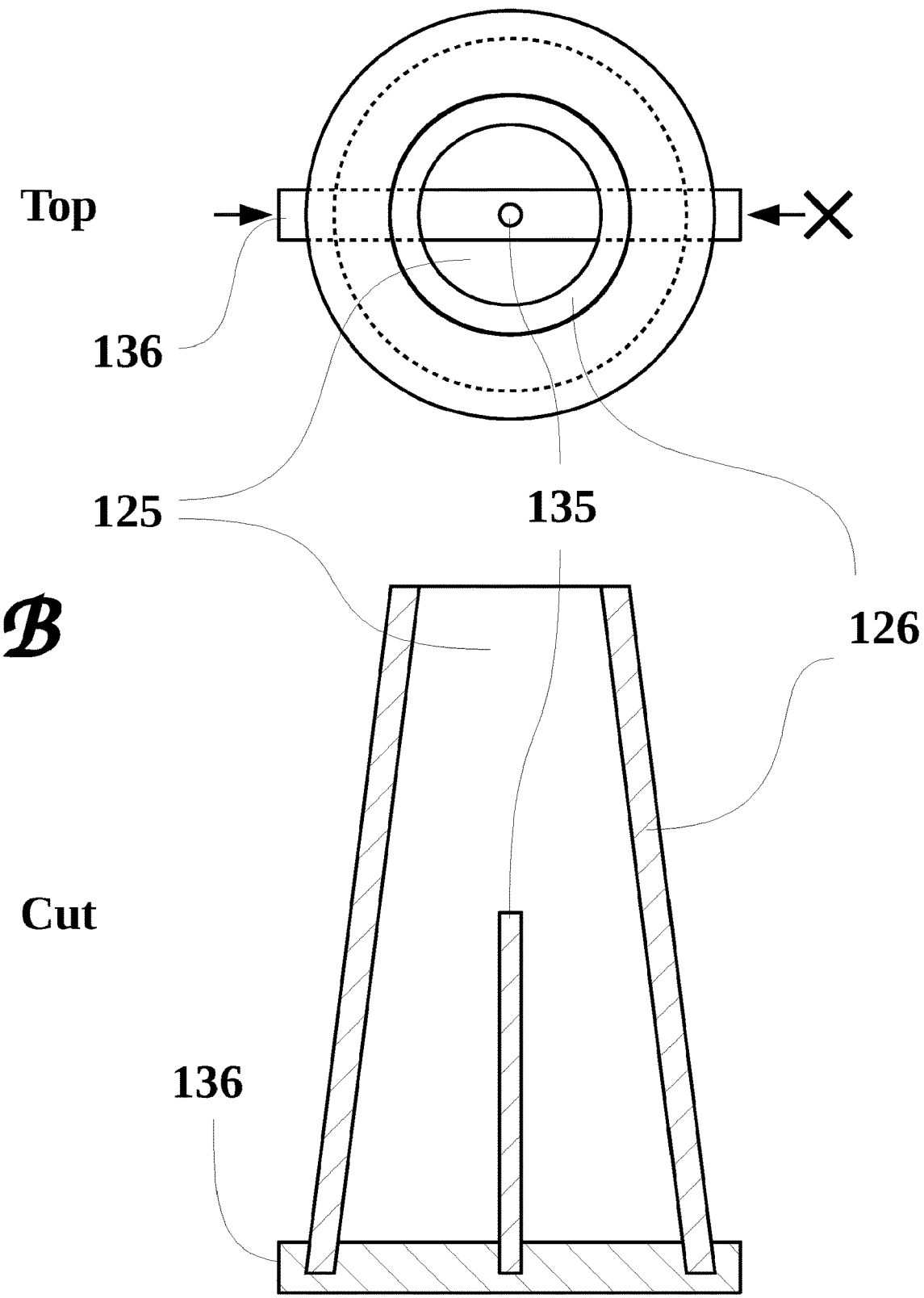

Fig 9A
137
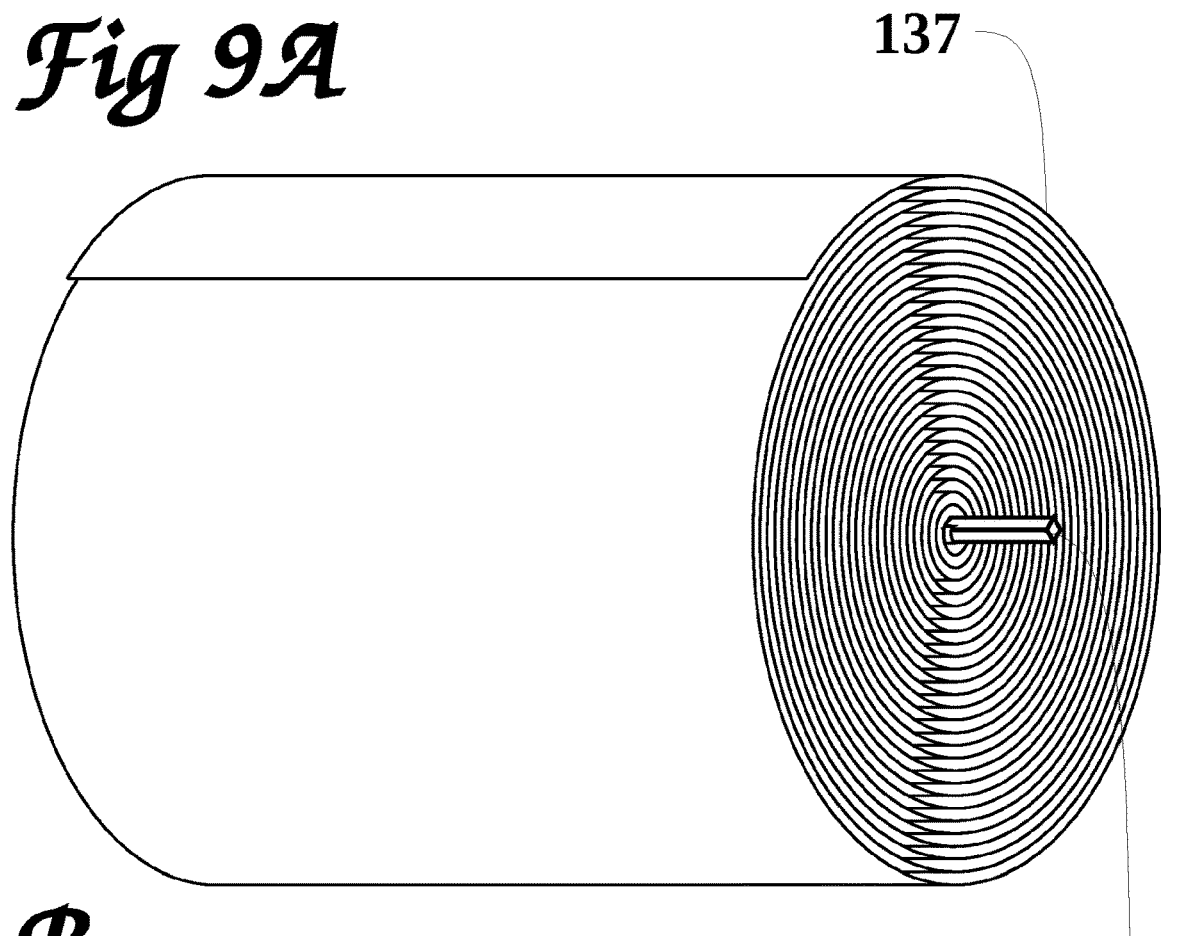
B  138
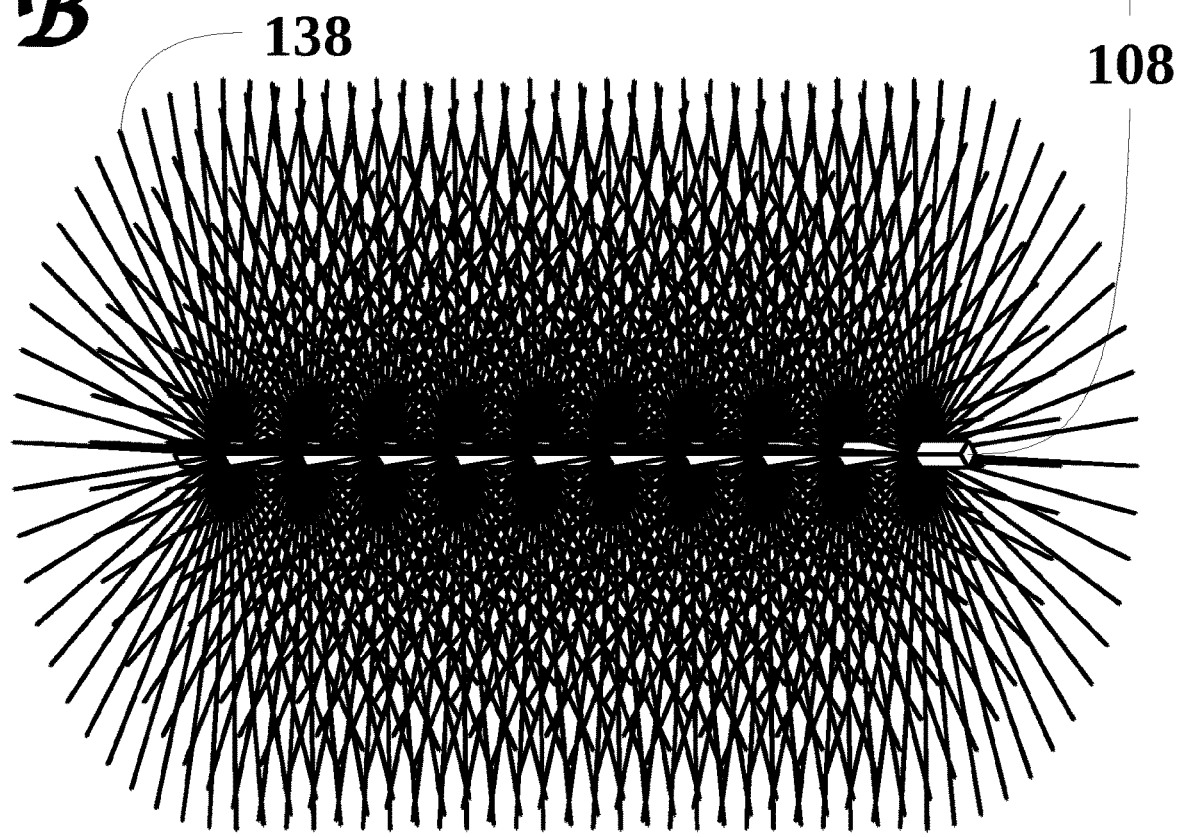
108

Fig 10A
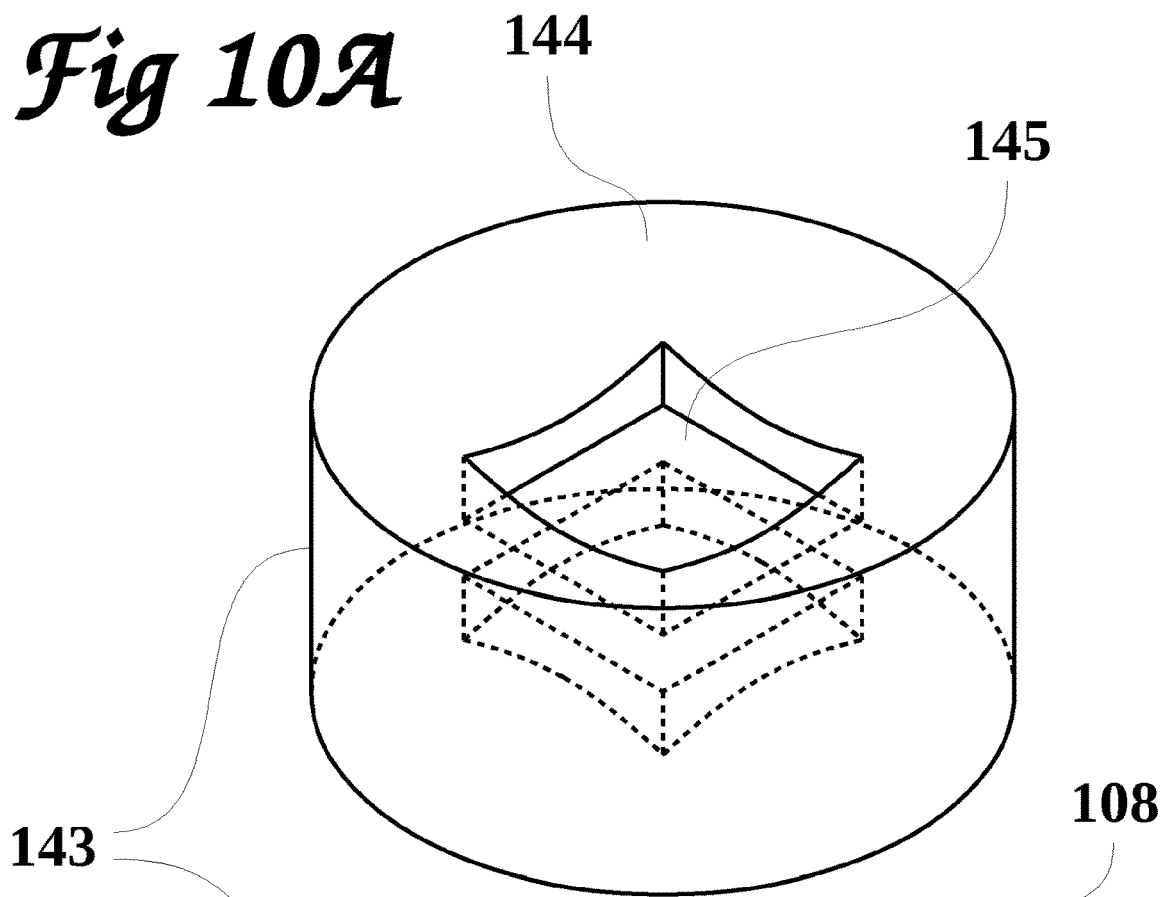
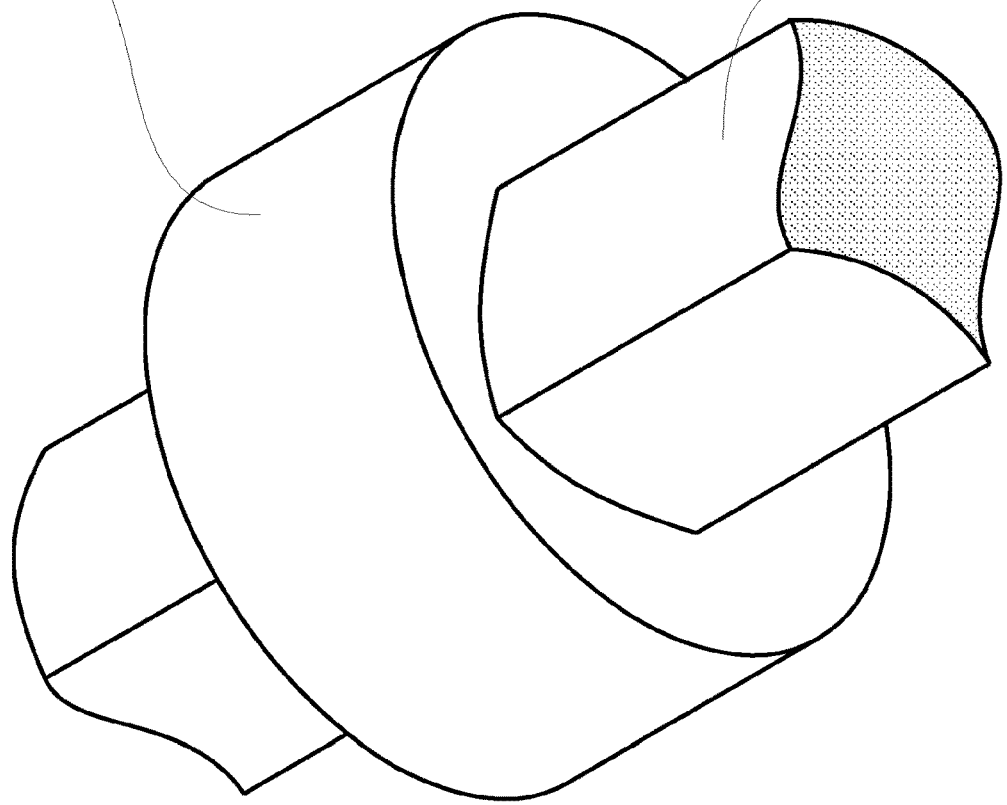

Fig 12A
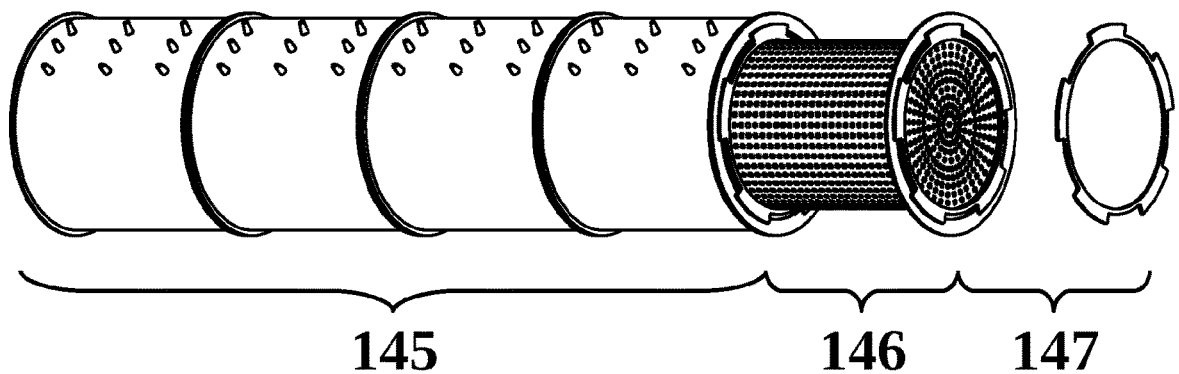
145    146    147
B
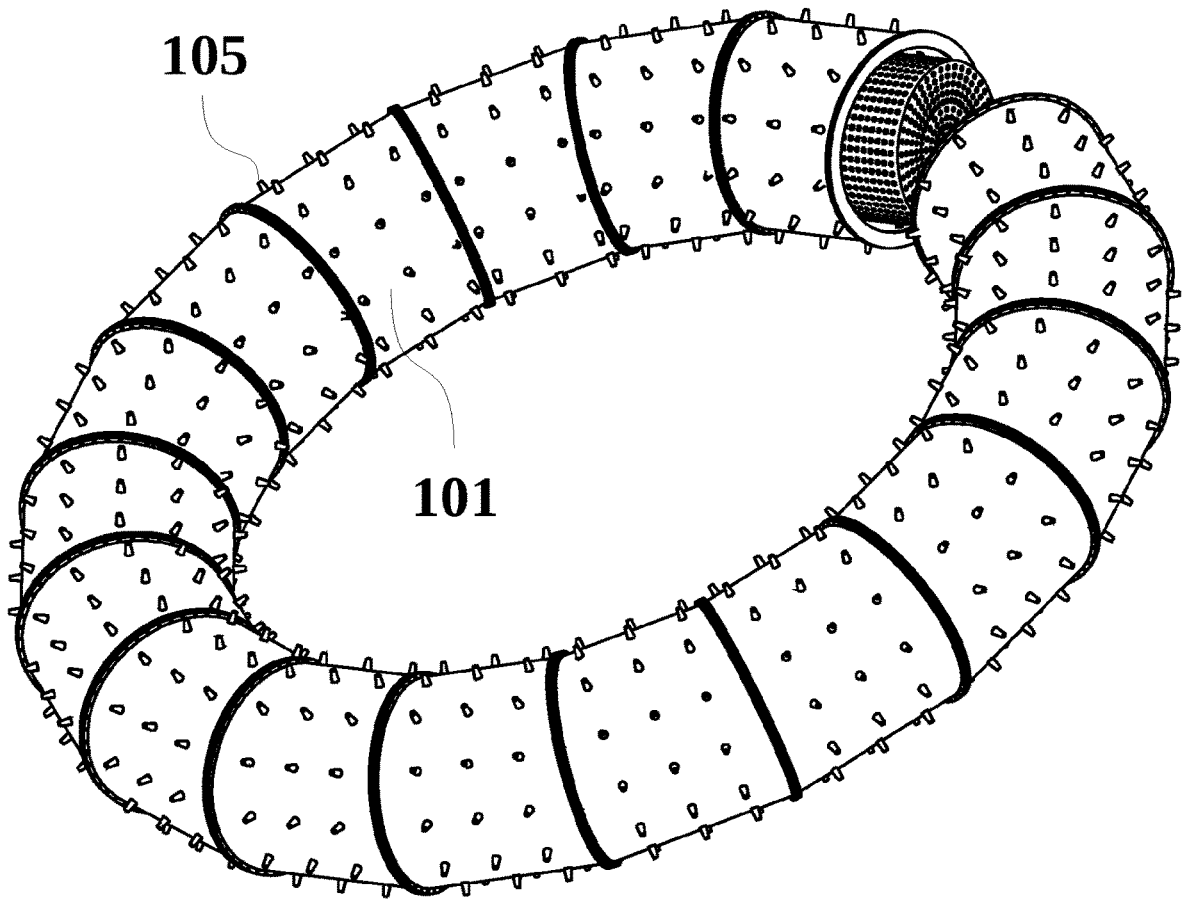
105
101

MULTI-PURPOSE BIO-ELECTRICAL MODULES AND PROCEDURES

CROSS REFERENCE TO RELATED APPLICATIONS

This application claims the benefit of U.S. provisional patent application Ser. No. 62/487,485 filed Apr. 20, 2017, and U.S. provisional patent application Ser. No. 62/492,163 filed Apr. 29, 2017, all by the present inventor which are incorporated by reference in their entirety.

TECHNICAL FIELD

The present invention relates to bio-electrical systems (BES), and more specifically to systems and methods used for microbial electrolysis.

BACKGROUND ART

Related Patents

| Patent Number | Kind code | Country Code | Issue Date | Patentee |
|---|---|---|---|---|
| 5,360,522 | A | US | 1994 Nov. 1 | Kuroda and Sakakibara |
| 5,443,706 | A | US | 1995 Aug. 22 | Kuroda and Sakakibara |
| 7,439,047 | B2 | US | 2008 Oct. 21 | Rozendal and Buisman |
| 7,709,113 | B2 | US | 2010 May 04 | Logan et al. |
| 7,922,878 | B2 | US | 2011 Apr. 12 | Logan |
| 8,002,955 | B2 | US | 2011 Sep. 23 | Daly and van Schaik |
| 8,124,259 | B2 | US | 2012 Feb. 28 | Rinzler et al. |
| 8,277,984 | B2 | US | 2012 Oct. 02 | Logan |
| 8,962,165 | B2 | US | 2015 Feb. 24 | Logan |
| 9,216,919 | B2 | US | 2015 Dec. 22 | Popat et al. |

Related Patent Application Publications

| Publ Number | Kind code | Country Code | Publ. Date | Patentee |
|---|---|---|---|---|
| 2012/0132521 | A1 | US | 2012 May 31 | Silver et al. |
| 2015/0259669 | A1 | US | 2015 Sep. 15 | May et al. |
| 2017/0166883 | A1 | US | 2017 Jun 15 | Deutzmann and Spormann |

Non-Patent Literature Documents

Bajracharya, S., Yuliasni, R., et al., (2017) 'Long-term operation of microbial electrosynthesis cell reducing $CO_2$ to multi-carbon chemicals with a mixed culture avoiding methanogenesis', *Bioelectrochemistry*, 113, pp. 26-34.

Faulkner, C. J. Lees, S., et al. (2008) 'Rapid assembly of photosystem I monolayers on gold electrodes', *Langmuir*, 24 (16), pp. 8409-8412.

Kuroda, M. and Watanabe, T. (1995) '$CO_2$ reduction to methane and acetate using a bio-electro reactor with immobilized methanogens and homoacetogens on electrodes', *Energy Conversion and Management*, 36 (6-9), pp. 787-790.

Laane, C. et al. (1984) 'Use of a bioelectrochemical cell for the synthesis of (bio)chemicals', *Enzyme and Microbial Technology*, 6 (4), pp. 165-168.

LaBarge, N.; Yilmazel, Y. D., et al., 2017 'Effect of pre-acclimation of granular activated carbon on microbial electrolysis cell startup and performance' *Bioelectrochemistry*, 113, pp. 20-25.

Nevin, K. P., Hensley, S. A., et al., (2011) 'Electrosynthesis of organic compounds from carbon dioxide is catalyzed by a diversity of acetogenic microorganisms' *Applied and Environmental Microbiology* 77 (9), pp. 2882-2886.

Siegert, M., Li, X., et al. (2015a) 'The presence of hydrogenotrophic methanogens in the inoculum improves methane gas production in microbial electrolysis cells', *Frontiers in Microbiology*, 5, Article 778, pp. 1-12

Siegert, M., Yates, M. D., et al. (2014) 'Comparison of nonprecious metal cathode materials for methane production by electromethanogenesis', *ACS Sustainable Chemistry & Engineering. American Chemical Society*, 2 (4), pp. 910-917.

Siegert, M. Yates, M. D., et al. (2015b) '*Methanobacterium* dominates biocathodic archaeal communities in methanogenic microbial electrolysis cells', *ACS Sustainable Chemistry and Engineering*, 3 (7), pp. 1668-1676.

Yahiro, A. T., Lee, S. M. and Kimble, D. O. (1964) 'Bioelectrochemistry: I. enzyme utilizing bio-fuel cell studies', *Biochimica et Biophysica Acta (BBA)—Specialized Section on Biophysical Subjects*, 88 (2), pp. 375-383.

Yehezkeli, O. et al. (2012) 'Integrated photosystem II-based photo-bioelectrochemical cells', *Nature Communications*, 3, pp. 1-7

BACKGROUND

Bio-electrical systems (BES) can be used for many purposes such as water treatment, energy recovery, energy storage, energy conversion, electrosynthesis, and so forth. Microbial electrolysis cells in wastewater treatment have the benefit of providing energy-neutral treatment. Numerous different reactor designs have been developed of which some are commercially available. Examples for such reactors are U.S. Pat. No. 7,709,113 (2010) to Logan or U.S. patent application 2012/0134521 (2012) by Silver et al. These BES cannot fully reap the benefits of this technology because much of the reactor volume is not used for the actual biological treatment reaction. Thus, cylindrical electrodes have been developed that utilize space more efficiently for biological reactions such as hydrogen production (U.S. Pat. No. 7,709,113 [2010] and U.S. Pat. No. 8,962,165, [2015], both to Logan, or U.S. Pat. No. 9,216,919, [2015] to Popat et al.), methane production, (Kuroda and Watanabe, 1995), or acetate production U.S. patent application 2015/0259669 [2015] by May et al.). Cylindrical designs are also popular for non-biological reactions, for example water sterilization (U.S. Pat. No. 8,002,955 [2011] Daly and van Schaik). There is a need for more versatile designs that can be used for many different applications.

Currently, BES are commercially used for wastewater applications in fixed installations where the gases produced are immediately fed back into the process. In such situations, land is often abundantly available and high pressure storage of the product not necessary. When pressurized storage or transport is needed, gas compressors are used which waste more energy compared with hydrostatic pressure generators. There is a need to collect produced gases at high pressure for further processing, or on unstable ground such as on ships, or under low gravity.

In wastewater treatment, anodic reactions are crucial in terms of treatment efficiency and kinetics and need to be maximized. This can be accomplished at the expense of cathodic surface as cheap materials such as steel provide sufficiently fast reaction kinetics. Flat or rod shaped electrodes in BES offer only a limited surface and surface areas are often comparable between anodes and cathodes (Kuroda and Watanabe, 1995; U.S. patent application 2012/0134521 [2012] by Silver et al.). This can be problematic for any catalytic process but in particular for biocatalytic processes where differences in surface areas between the two electrodes should be in orders of magnitude. Tubular reactor designs offer a good solution for this problem by making the surface of one electrode asymmetrically large (U.S. Pat. No. 7,922,878, [2009] to Logan, or U.S. Pat. No. 9,216,919, [2015] to Popat et al.). One electrode can be inserted into another which further reduces the overall volume of BES, for example U.S. Pat. No. 8,962,165 (2015), to Logan. High surface area electrodes have been developed to improve their surface-to-volume ratios. They can contain lose graphite fibers inside their anodic compartments, as, for example, U.S. Pat. No. 8,125,259 (2012) to Rinzler et al. teaches, or have graphite fibers attached to a current collector forming a graphite fiber brush as in U.S. Pat. No. 7,922,878 (2011) to Logan. The same inventor also provided electrodes which are porous packages that are permeable to microorganisms as demonstrated by his U.S. Pat. No. 8,277,984 (2012). Such packages as well as fiber-filled electrodes have a higher surface-to-volume ratio, but they have suffer from poor electrical contact. The mentioned fiber brushes provide better electrical contact and can be inserted into another electrode but are less versatile with lower surface-to-volume ratio. There is still a need for improvement of BES electrodes.

Bio-electrical processes often proceed via cascaded chemical or biochemical reactions where the product of one process serves as substrate for another. Examples for intermediates in BES are hydrogen gas (U.S. Pat. No. 5,360,522 [1994] to Kuroda and Sakakibara), acetic acid (U.S. patent application 2015/0259669 [2015] by May et al.), formic acid, carbon monoxide (U.S. patent application 2017/0166883 [2017] by Deutzmann and Spormann), and so forth. These intermediates may be further processed in consecutive reactions, for example to methane gas or organic compounds (Bajracharya et al., 2017). For example, acetate can be produced using hydrogen formed in the reactor. Then, this acetate may be used in a subsequent reaction by other microorganisms to form biofilms. Such biofilms, in turn sometimes accumulate useful polymers. The addition of electrochemical methods allows better control of the various steps involved in such cascaded reactions, such as the production of the aforementioned intermediates. It is necessary to improve the production and transport of substrates and products in BES.

The electrochemical potential in BES is determined by the redox potentials of substrates, products, and their concentrations. It is described in the Nernst equation:

$$E = E_0 + \frac{RT}{zF} \ln\left(\frac{C_{red}}{C_{ox}}\right) \quad (1)$$

where E is the equilibrium potential of the reaction, $E_0$ is the standard potential at a temperature of 298 K, and all concentrations are 1 M or 1 bar. R is the universal gas constant (8.31 J K$^{-1}$ mol$^{-1}$), T is the temperature, z is the number of electrons transferred, F is the Faraday constant (9.64·10$^{-4}$ C mol$^{-1}$), $C_{red}$ is the concentration of the reduced form of the reacting compound, and $C_{ox}$ is the concentration of the oxidized form of the reacting compound. In BES, there is often a multitude of various compounds involved in the process. In contrast, only one product, such as methane (U.S. Pat. No. 5,360,522 [1994] to Kuroda and Sakakibara) or hydrogen gas (U.S. Pat. No. 7,439,047 [2008] to Rozendal and Buisman) may be collected. To allow stable production of one compound at constant rates the electrochemical potential needs to be better controlled. This is accomplished by means of instruments called potentiostats. However, such potentiostats are usually expensive and power consumption is within a specific range which is not scalable.

BES often require biological seeds such as microorganisms acting as catalysts (U.S. Pat. No. 5,360,522 [1994] to Kuroda and Sakakibara). These bio-catalysts carry out highly specific reactions. In case of microorganisms, such bio-catalysts often slowly propagate (Siegert et al., 2015a; Bajracharya et al., 2017). Slow propagation throughout the BES stretches startup time which leads to economic losses. Using electrodes and seeds which have been pre-acclimated to electrophilic microorganisms can accelerate the startup process (Siegert et al., 2015b; LaBarge et al., 2017). However, seeding BES needs to be further improved.

Various types of biological materials catalyze bio-electrical reactions. Such materials can be enzymes, their catalytic centers, or entire biological cells. Examples for enzymes are glucose oxidases, amino acid oxidases, and alcohol dehydrogenases (Yahiro et al., 1964), hydrogenases or dehydrogenases (Yue and Lowther, 1986), peroxidases (Laane et al., 1984), photosystem I (Faulkner et al., 2008) and photosystem II (Yehezkeli et al., 2012), and many more. Biological cells typically used in bio-electrical reactions can be found in many domains of life but most have been identified as prokaryotes. Examples for prokaryotes carrying out bio-electrical reactions are plentiful, but to name a few, they can belong to genera such as *Propionibacterium, Sporumusa, Clostridium, Actinobacillus, Escherichia, Desulfovibrio, Desulfococcus, Sulfurospirillum, Methanobacterium, Methanobrevibacter, Methanothermobacter, Methanospirillum, Methanocalculus, Methanococcus, Methanosarcina, Geobacter, Shewanella, Chlorella, Anabaena, Calothrix, Pseudanabaena, Nostoc, Synechococcus, Synechocystis, Lyngbya, Arthrospira*, and many more. In some case, combinations of biological cells, enzymes, or non-biological catalysts are possible as well (Siegert et al., 2015a and Siegert et al., 2014). Some applications require pure biological catalysts (Nevin et al., 2011) while others work well with mixed cultures or cultures enriched in some community members (Siegert et al., 2015a). Due to the enormous diversity of possible combinations of BES, there is no good system that is versatile enough to accommodate many different applications.

Granular or powder-based electrodes usually suffer from high electrical resistance. This can be overcome by compressing the electrode material to improve electrical contact between particles. However, compressing electrode material reduces pore space and inhibits mass transport. It is necessary to find the right balance between good electrical contact and sufficient pore space.

BRIEF SUMMARY OF THE INVENTION

In one embodiment, a tubular bio-electrical system (BES) is provided comprising an outer electrode, an inner electrode, and controllable gas outlets. The outer electrode of the BES is also the housing of the BES. The inner electrode is filled with active biological material. Seeding methods for both electrodes are provided. The volumetric flow of electrolyte passing each electrode can be controlled using integrated shutters for each electrode. The invented BES is modular and each module can be controlled by an electrochemical algorithm.

Advantages

In accordance with the tubular design, the BES can be operated at higher hydrostatic pressures than current systems, saving energy and space for pressurizing produced gases. It can be serialized and parallelized for a wide range of applications. Its general design is suitable for applications on unstable ground or under zero-gravity. This design also allows easier temperature control. Some procedures included facilitate maintenance and reduce startup time. These and other aspects will become apparent from a consideration of the ensuing description and accompanying drawings.

BRIEF DESCRIPTION OF DRAWINGS

FIG. 2 A, Exploded depiction of one segment of a bio-electrical reactor system, B, Assembled segment of bio-electrical reactor.

FIG. 3 Outer electrode with A, seeding thread on the electrode surface, B and C, seeding thread on the holder surface.

FIG. 4 A, assembled float switch of gas outlet with embodied high sensitivity floater, B, gas outlet of float switch, C, embodiment of the floater with medium sensitivity, providing contact in float switch.

FIG. 5 A, Inner electrode drum, B, partial cut of the inner electrode.

FIG. 6 A, front and B, perspective views of holder of inner electrode with C being a modified holder with inner shutter blades.

FIG. 7 Example of outer electrode with flange insulator, A, exploded depiction of the flange assembly, B, longitudinal section through one bolt hole of the assembled flange.

FIG. 8 Gas outlet with integrated conductivity sensor.

FIG. 9 A, inner electrode coiled embodiment, B, Inner electrode electrode embodiment with contact appendages extending from the shaft.

FIG. 10 Joint for two shafts and assembled view with front and rear electrode shaft.

FIG. 12 A, Assembled serial configuration of a segmented in the form of a tube., B, Assembled serial configuration of a segmented reactor in the form of a ring.

DRAWINGS—REFERENCE NUMERALS

Figure 1:
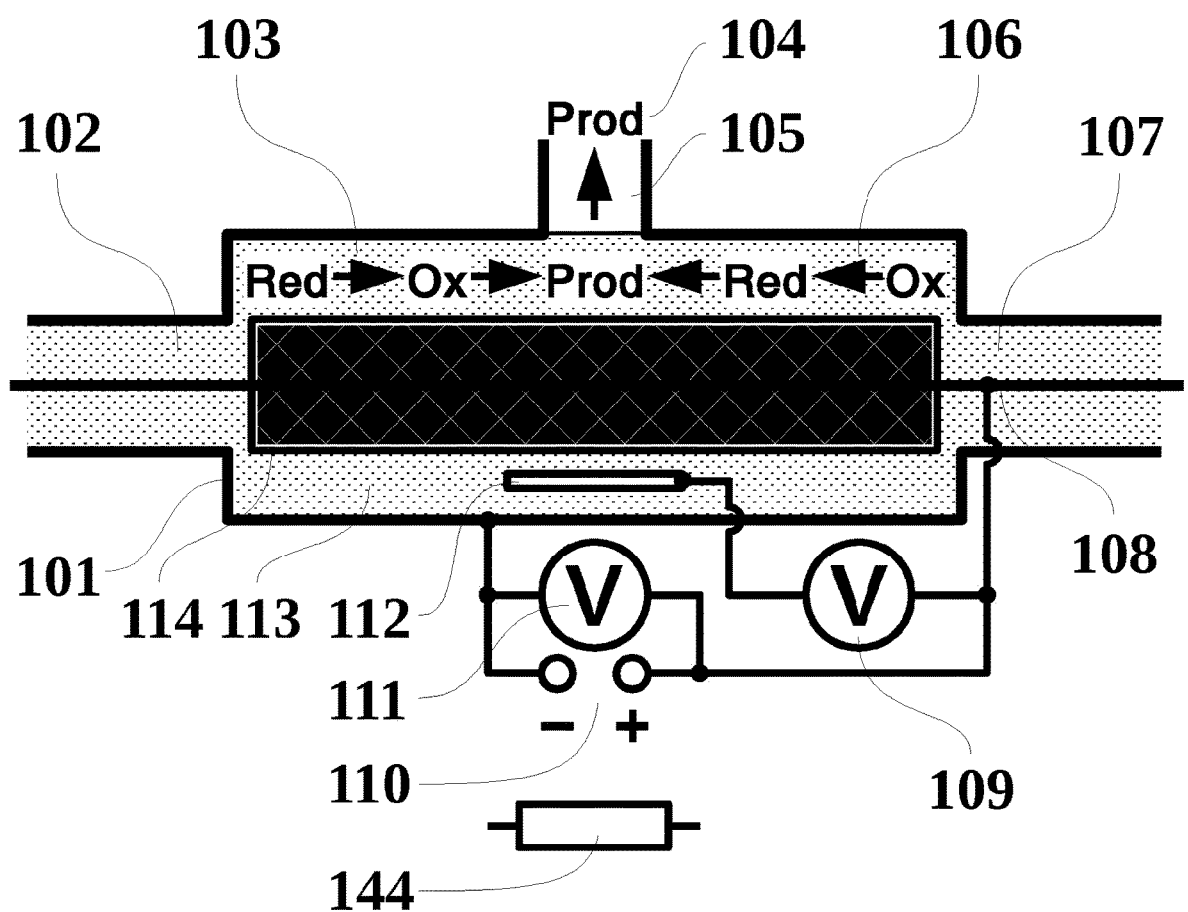
FIG. 1 Schematic of a bio-electrical cell; Red, reductant, Ox, oxidant, Prod, product.

101 Housing electrode
102 Electrolyte inlet
103 Oxidation reaction
104 Gaseous product
105 Gas outlet
106 Reduction reaction
107 Electrolyte outlet
108 Inner electrode shaft
109 Voltmeter between the reference electrode and the inner electrode
110 DC power supply
111 Voltmeter between the inner and the outer electrode
112 Optional reference electrode
113 Electrolyte
114 Inner electrode
115 Gasket
116 Flange
117 Shutter blade
118 Inner electrode holder
119 Central longitudinal rotation axis
120 Through hole
121 Electrode holder seeding gap
122 Outer electrode wall seeding gap
123 Attachment line
124 Floater
125 Gas outlet hollow
126 Gas outlet wall
127 Floating body
128 Conductive surrounding
129 Pore hole of the inner electrode
130 Electrode holder sidearm
131 Electrode holding central opening
132 Sidearm opening of electrode holder
133 Exploded view of the flange insulation ring configuration
134 Flange insulation ring
135 Gas outlet inner conductivity probe
136 Gas outlet holder of inner conductivity probe
137 Coiled inner electrode
138 Appendage
139 Inner shutter disc
140 Sidearm opening of inner shutter
141 Inner shutter sidearm
142 Inner shutter central hole
143 Shaft joint
144 Lead-in concave
145 Center pocket
146 Electrical load when operated as fuel cell
147 Complete segments 1 to 4 of the serial BES configuration
148 Segment 5, without the outer electrode
149 Segment 6, with holders only

DISCLOSURE OF INVENTION

First Embodiment

Outer Electrode

A BES is provided comprising an outer electrode 101 and an inner electrode 114 as depicted in the schematic FIG. 1. An exploded drawing of the BES is shown in FIG. 2A, an assembled BES is shown in FIG. 2B, and its operation is described in the section OPERATION. The shape of the BES in FIG. 2A is cylindrical or tubular and the outer electrode 101 is identical with the housing of the BES. That is, the housing and the outer electrode are also tubular. The outer electrode 101 is made of an electrically conductive material such as steel. The diameter and length of the outer electrode are 2 m each. The BES has two openings 102 and 107 in horizontal direction which are shown in FIG. 1 and FIG. 3A. Gases can be collected on top of the BES using clusters of gas outlets 105 as shown in FIG. 1 and FIG. 2A.

Float Switch

Each one of the gas outlets 105 in FIG. 1 is a float switch which encompasses a floater 124 and a housing 126 as shown in FIG. 4A. Perspective, Top and Side views of the float switch housing or wall 126 are depicted in FIG. 4A and FIG. 4B. As shown in FIG. 4B, the float switch housing is of conical shape with an electrically conductive wall 126. The wall of the float switch encloses a hollow 125 into which the floater 124 (FIG. 4A) is inserted. The floater is illustrated in FIG. 4C. The floater comprises two components: the actual floating body 127 and an electrically conductive surrounding 128. This electrically conductive surrounding is made of conductive blades which adhere to the surface of the floating body 127. These blades are made of conductive material such as graphite. They are spaced away from each other so as to allow passage of gas or liquid into the hollow 125 shown in FIG. 4B. The floater itself is attached to the gas outlet by an attachment line 123 as shown in FIG. 4A. The gas outlets 105 are screwed into through holes 120 of the outer electrode 101, as shown in FIG. 3A. The distance between the gas outlets is 30° in tangential direction and ⅓ of the length of the BES in longitudinal direction.

Inner Electrode

An inner electrode 114 is placed inside the outer electrode 101 as shown in FIG. 1 and FIG. 2A. The inner electrode 114 is a hollow tube or cylinder as illustrated in FIG. 5A and in the partial cut in FIG. 5B. The wall of the inner electrode is made of titanium. It is made porous by holes 129. The hollow space of the inner electrode is filled with electrically conductive material such as graphite granules. This filling material simultaneously provides support for biological catalysts. The holes 129 in FIG. 5A are of such size that the filling material is retained while allowing percolation of the electrode 114. Retention of filling material can also be accomplished by adding an additional layer of wire mesh or cloth. The distance between the holes and the thickness of the electrode wall are chosen according to commonly used pipe standards. A shaft 108 is inserted into the center of the inner electrode 114 as illustrated in FIG. 5A and FIG. 5B. The shaft is structurally connected and in electrical contact with the inner electrode. The cross section of the shaft is of rectangular shape. The shaft also connects the electrode electrically with the DC power supply 110 shown in FIG. 1. As shown in FIG. 5B, the shaft 108 is inserted entirely.

Inner Electrode Holder and Shutter Blades

The inner electrode 114 is held inside the outer electrode 101 by a holder 118 as illustrated in the exploded FIG. 2A and the assembled FIG. 2B. The holder fixes the distance between the inner electrode 114 and the outer electrode 101 to be between 1-5 cm. One or more inner electrode holders 118 embrace the inner electrode 114 as depicted in FIG. 2A. As shown in FIG. 6A and FIG. 6B, the electrode holder has sidearms 130 which have the same length and which space the inner electrode 114 (FIG. 5A) at a constant distance away from the outer electrode 101 (FIG. 3A). FIG. 6A and FIG. 6B show that the holder also has a central opening 131 of the same diameter as the inner electrode 114 (FIG. 5A). The sidearms are arranged so that there is an opening 132 between them. As shown in FIG. 2A, shutter blades 117 are attached to the outer electrode 101, matching the size and number of the sidearms 132 (FIG. 6A) of the holder 118. Each shutter blade covers at least the entire area of one of the sidearm openings of the holder. The shutter blades are made of the same material as the outer electrode and attached to it by welding.

Flange Insulation

The outer electrode 101 of the BES has ordinary flange connectors 116 with bolt holes as shown in the partial explosion 133 of FIG. 7A. As shown in FIG. 2A, FIG. 2B, and FIG. 7A, gaskets 115 can be used. The gasket material is electrically insulating, for example non-conductive plastic, rubber, or similar. In the embodied bolted flange, shown in FIG. 7A, metallic bolts are used. An additional layer of insulating material or flange insulator 134 covers at least the entirety of the surface which would be in direct electrical contact with nuts, bolts, and washers as shown in FIG. 7B. The flange insulator provides an additional layer of insulation inside the bolt holes and the proximal side of the flange. These bolt insulators are connected by a ring matching the flange as shown in FIG. 7A. The insulating ring and bolt insulators are made of the same insulating material.

Operation and Best Mode of Carrying Out the Invention

General Operation

The invented BES is best used for energy efficient wastewater treatment. Thus, the purpose of the embodied BES shown in FIG. 1 is the production of a methane gas mixture 104 on the outer electrode 101, which is operated as cathode. Hydrogen gas may be produced as a byproduct in trace amounts not exceeding 50%. At the same time, the BES removes harmful organic compounds from wastewater by oxidation on the inner electrode 114, which is operated as anode. A reduction reaction 106 takes place on the cathode 101, which converts $CO_2$ to methane gas. Electrons for $CO_2$ reduction are derived from organic matter which is oxidized on the inner electrode 114. These electrons are accepted by the anode and travel along electrical conduits such as wires or cables to the outer electrode 101 as shown in the schematic FIG. 1. The carbon for methane production is derived from the $CO_2$ produced on the inner electrode 114 or from the $CO_2$ already contained in the electrolyte 113 in FIG. 1. Dissolved $CO_2$ can be in the form of carbonic acid. Methane gas is produced by reacting $CO_2$ with hydrogen produced at the cathode or produced by material interacting with the cathode according to:

$$CO_2 + 4H_2 \rightarrow CH_4 + 2H_2O \tag{2}$$

Hydrogen gas ($H_2$) represents one possible intermediate reducing agent.

Float Switch

Gas is collected on top of the BES using the gas outlets 105, shown in FIG. 1 and FIG. 2A, which are operated as float switches shown in FIG. 4A. The BES is operated horizontally in flow-through mode as depicted in FIG. 2B. That is, the electrolyte is moved through the BES in longitudinal direction. This operation allows gas collection on top the of the BES while moving the electrolyte in horizontal reaction, thereby separating gas from liquid taking advantage of different densities. As detailed above, the float switches 105 FIG. 4A, each comprising the conical wall 126 (FIG. 4A and FIG. 4B) and the floater 124 (FIG. 4C) shown in FIG. 4A. The floater has a conductive surrounding 128, shown in FIG. 4C, which allows electrical contact with the wall 126 (FIG. 4B) once the floater penetrates the outlet deep enough, depending on the level of liquid. It is important that liquid and gas can pass the floater to prevent plugging of the float switch.

The BES is operated as a closed system under pressure. A pressure regulated valve attached downstream of the gas outlet releases produced gas at the desired pressure. In the embodied BES, the pressure valve releases accumulated gas above 1.7 MPa but the pressure may be lower or higher than that, depending on the specific situation in which the BES is operated. Pipeline pressure may be higher and intermittent storage pressure may be lower, or vice versa. It is important to operate the BES under lower hydrostatic input pressure than the desired gas output pressure because gas production increases the pressure of the entire system.

Inner Electrode

In FIG. 2A, the embodied inner electrode 114 is porous to allow percolation of the electrode by the electrolyte 113 (see FIG. 1). The porosity of the inner electrode also permits electrolytic connection with the outer electrode 101. In FIG. 5A and FIG. 5B, the inner electrode 114 is a drum to be filled with material that is electrically conductive providing support for biological catalysts. The filling is electrically connected to the housing of the inner electrode 114 and to the shaft 108 of the inner electrode, shown in the cut of FIG. 5B.

The shaft 108 of the inner electrode 114 allows rotation of the entire electrode around the central longitudinal axis 119 by rotating the shaft, as shown in FIG. 2A. Rotating the inner electrode also positions the electrode holders 118. Positioning the electrode holders moves the sidearm openings 132 of the holders (for better detail see FIG. 6A) towards the shutter blades 117 permitting regulation of the electrolytic flow between the inner and outer electrodes. As the shutter blades move towards the sidearm gaps of the holders 132 in FIG. 6A, electrolytic flow is down-regulated and ultimately stopped. The electrode holder has a central opening 131 for insertion of the inner electrode 114 (FIG. 5A). The central placement of the opening ensures a constant distance between inner 114 and outer electrode 101 in FIG. 2A and FIG. 2B. The constant distance between the inner and the outer electrode enables a spatially even distribution of redox gradients.

Seeding

The provided BES facilitates application of biological catalysts. For example, the inner electrode 114 in FIG. 5A has the shape of a drum with and inner compartment that can be filled, as illustrated in the partial cut in FIG. 5B. The filling material is conductive and catalytically active. The filling material carries the active biological catalyst and has the shape of granules, flakes, powder, rods, and so forth. Conductivity and activity is improved by the biological catalyst. Applying a pretreated inoculum to the inner electrode 114 (FIG. 5A) together with the filling material accelerates startup time. For example, a mix of seeding material and un-seeded material can be approximately 1/10. Other ratios are possible as well, for example 1/100 or 1/1.

Biological compounds attached to the electrode surfaces of the outer electrode 101, the inner electrode 114, or dispersed in the electrolyte 113 catalyze the respective redox reactions 103 and 106 in FIG. 1. Such biological compounds can be a mixture of biological electrophilic cells, for example prokaryotic or eukaryotic cells. The electrophilic cell mixture is provided by the wastewater being treated or by a concentrated seed or inoculum which can be a liquid cell suspension or an agglomeration of the biological cells for example biofilms, filaments, tissue, and so forth. Examples for electrophilic prokaryotic cells contained in the inoculum are *Propionibacterium, Sporumusa, Clostridium, Actinobacillus, Escherichia, Desulfovibrio, Desulfococcus, Sulfurospirillum, Methanobacterium, Methanobrevibacter, Methanothermobacter, Methanospirillum, Methanocalculus, Methanococcus, Methanoculleus, Methanocorpusculum, Methanosarcina, Geobacter, Shewanella, Chlorella, Anabaena, Calothrix, Pseudanabaena, Nostoc, Synechococcus, Synechocystis, Lyngbya, Arthrospira*, and many more. Examples for eukaryotic cells are tissue or fungi (e.g. *Aspergillus*) including yeasts, (e.g. *Saccharomyces* or *Candida*).

Electrical Control

As illustrated in FIG. 1, the BES is connected to a DC power source 110 establishing electrical contact between the outer electrode 101 and the inner electrode 114. The DC power source also drives the reactions 103 and 106 on both electrodes by providing a stable electrochemical potential. The DC power source converts AC input voltage to the required DC output voltage. AC power is provided by a gas turbine which uses the methane gas mixture 104 produced by the BES. This power converter is henceforth called DC power supply. The DC power supply is software controlled by an algorithm that is a feedback loop reading the electrochemical potential between a reference electrode 112 and the inner electrode 114. The feedback loop then adjusts the voltage between the inner and the outer electrode according to the equation:

$$\frac{U_m}{E_m - E_{off}} = \frac{U_n}{E_{SP} - E_{off}} \qquad (3)$$

where $U_m$ is the most recent measured cell voltage between the inner and the outer electrode, measured by a voltmeter 111 shown in FIG. 1. $E_m$ is the last measured potential between the reference electrode and the inner electrode, measured by a voltmeter 109. $E_{off}$ is an optional offset potential set by the user. $U_n$ is the new cell voltage between the anode and the cathode, and $E_{SP}$ is the setpoint potential between the reference and the inner electrode. The offset potential $E_{off}$ ensures that the cell voltage $U_n$ can be set correctly when noise interferes, for example when the calculated $U_n$ would be within the noise range.

Description of Additional Embodiments

Outer Electrode

In the first embodiment, the outer electrode 101 is tubular or cylindrical, as shown in FIG. 2A. In other embodiments, the outer electrode 101 in FIG. 1 may be of conical shape or of tubular shape with conical parts. The outer electrode can have various dimensions. It can be 2 cm diameter by 5 cm length. It can also be 2 m by 2 m or 0.5 m by 5 m. The scalable design also allows larger or smaller dimensions, for example in cm range. In the first embodiment, the outer electrode 101 in FIG. 1 is made of steel. In alternative embodiments, the outer electrode is made of a different electrically conductive material such as titanium, brass, gold, platinum, copper, carbon, composite materials, or similar. The outer electrode electrode 101 may be made of carbon, ceramics, fiber glass, zeolite, pumice, and so forth, which can be made electrically conductive, for example by coating, doping, or other methods. In an additional embodiment, the outer electrode may be coated by an extra outside layer of electrical insulation, for example plastic foil, ceramics, electrical tape, insulating paint, and so forth.

Gas Outlets/Float Switches

Depending on the application, multiple gas outlets 105 can be arranged in radial and/or longitudinal clusters, as shown in FIG. 2A. The gas outlets are typically placed on top of the horizontal reactor. While the angle of the interval in which the gas outlets are placed is application specific, a typical radial range may be between 10° and 30°. In horizontal direction, the distance between the gas outlets may be ⅓ to 1/10 of the length of the BES. Typically, the gas outlets are screwed into the through holes 120 shown in FIG. 3. In further embodiments, gas outlets can be soldered, welded, or latched onto or into the through holes. In the first embodiment, nine gas outlets 105 are placed on the outer electrode 101, as shown in FIG. 2A and FIG. 2B. In further embodiments, more or less than nine gas outlets can be placed in either direction. In alternative embodiments, there may be no gas outlets at all or gas outlets are placed all over the BES.

In the first embodiment, the gas outlet 105 (FIG. 1) is also the float switch shown in FIG. 4A. This float switch 105 has a conical housing 126, shown in FIG. 4A and FIG. 4B. In other embodiments, the gas outlet is not a float switch or of cylindrical shape. In further embodiments, the conductive surrounding 128 of the floater 124 is made of blades covering the length of the floater only partially, for example as shown in FIG. 4D. In further embodiments, the surrounding is made of wire mesh, cloth, gauze, or other porous material which covers the floating body at least partially. The surrounding material can be metal or metal alloys, such as steel, titanium, copper, gold, platinum, and so forth. It may also be of non-metal material such as graphite, carbon cloth, conductive polymers, and so forth. In alternative embodiments, the floater may lack a separate surrounding and it may be made entirely of a more uniform electrically conductive material such as graphite, carbon cloth, a conductive polymer, and so forth.

In alternative embodiments, the gas outlet 105 (FIG. 1) is not the float switch shown in FIG. 4A. Then, other means of gas-liquid separation such as frits, gauze, membranes, or other porous separators are used. In other embodiments, an electric conductivity sensor can be used, as shown in FIG. 8A and FIG. 8B. The conductivity sensor is integrated in the gas outlet by placing a conductive probe 135 inside the gas outlet, which is attached to the outlet using an insulating holder 136. The inner probe can be made of the same material as the outlet, for example steel, but also of any other electrically conductive material such as gold, platinum, titanium, carbon, and so forth. The insulating probe holder 136 may be made of plastic, rubber, glass, and so forth. It may be attached to the gas outlet using a thread, by latching, gluing, and so forth.

Inner Electrode

In the first embodiment, the inner electrode 114 is of cylindrical shape with radius and length smaller than that of the outer electrode 101 as shown in FIG. 2A. The inner electrode 114 is fully inserted into the outer electrode as shown in the assembled FIG. 2B. In alternative embodiments, the inner electrode is partially inserted into the outer electrode or the length and diameter of the inner electrode may be much shorter than those of the outer electrode. In further embodiments, the inner electrode may also have another shape which approximately matches the shape of the outer electrode 101 (FIG. 3A). In yet further embodiments, the shape of the inner electrode does not match the shape of the outer electrode at all. For example, the inner electrode and the outer electrode may be of different cross section geometries and may be triangular, rectangular, hexagonal, octagonal, cross-shaped, star-shaped, and so forth.

In the first embodiment, the inner electrode 114 in FIG. 5A is made of titanium. In alternative embodiments, the inner electrode may also be made of materials such as carbon, ceramics, fiber glass, zeolite, pumice, and so forth, which can be made electrically conductive, for example by coating, doping, or other methods. As shown in FIG. 5A, the wall of the embodied inner electrode 114 itself is porous. In one embodiment, the pores may be simple the holes 129 punched or drilled into the electrode wall. In other embodiments, the pores may be spaces between wires of a wire mesh, pores between fibers of a cloth, or pores of a material such as membranous material, ceramics, fiber glass, zeolite, pumice, and so forth. In further embodiments, combinations of different materials are possible. For example, cloth may be attached to the wall made of wire mesh. Pore sizes and numbers can vary to great extend depending on the application. Punched, drilled, or mesh pores may between 1 µm and 100 cm. Pores of ceramics or membranes may be much smaller than that, for example nm or Å.

In alternative embodiments, the inner electrode 114 in FIG. 1 may be a spiral comprised of one or more coiled sheets 137 as shown in FIG. 9A. In further embodiments, the inner electrode is a solid cylinder such as a rod. In yet further embodiments the inner electrode may be a brush with electrically conductive appendages 138 as shown in FIG. 9B. I may also be made of gauze, or any other geometry that can be inserted into the outer electrode. The sheets 137 in FIG. 9A as well as alternative geometries may be wire mesh, gauze, or fabric made of metals such as titanium, platinum, copper, and so forth. The material may also be metal alloys like steel, brass, or similar. The sheets 137 may also be made of carbonaceous material like carbon felt, carbon cloth, and so forth.

In the first embodiment, the filling of the inner electrode 114 (FIG. 5A and FIG. 5B) is particulate matter such as granules, powder, fibers, flakes, rods, and so forth. In other embodiments, the filling can be filamentous material such as cloth, gauze, mesh, and so forth. In still other embodiments, the filling can be particulate or filamentous polymers such gels, plastics, rubber, and so forth. In some embodiments, the filling can be made of carbon (e.g. graphite or carbon black), minerals (e.g. zeolites or pumice), organic or inorganic polymers (e.g. plastic or silicone), metals, or metal alloys such as steel, titanium, platinum, and so forth. In further embodiments, combinations of fillings are possible as well. In some embodiments, the filling can be made of ceramics, fiber glass, zeolite, pumice, or other porous material which may be made conductive, for example by coating, doping, or other methods. The catalyst coating the surface of the filling material can by biological material such as cells or enzymes or it can be non-biological material such as platinum, ruthenium, cobalt minerals, and so forth.

Shaft

In the first embodiment, the electrical connection of the DC power supply 110 with the inner electrode 114 is provided by connecting the shaft 108 of the inner electrode as shown in FIG. 1. The shaft is inserted through the center of the distal discs of the inner electrode 114 as shown in FIG. 5B, thereby establishing electrical contact with the wall. In another embodiment, the shaft may be off-centered. The shaft may have different cross section geometries such as rectangular, triangular, hexagonal, octagonal, circular, cross-shaped, star-shaped, and so forth. In yet further embodiments, there may be more than one shaft inserted concentrically, or otherwise. In other embodiments, that shaft is partially inserted.

In further embodiments, appendages such as filaments, wires, or fibers 138 may be connected to the shaft 108 as illustrated in FIG. 9B. These appendages together with the shaft may form a brush, similar to that shown in FIG. 9B, which is an electrode itself. The brush may be inserted into the electrode 114 shown in FIG. 5A. The appendages 138 in FIG. 9B are made of electrically conductive material like the inner electrode 114, the shaft 108, or the filling in FIG. 5A. In further embodiments, the appendages are made electrically conductive by coating, doping, or other methods. In other embodiments, the shaft, the inner electrode, and the filling material may be made of different materials. In some embodiments, the appendages 138 in FIG. 9B are hollow. In further embodiments, the appendages 138 and the shaft 108 are hollow. In yet further embodiments, other or additional appendages may be reaching into the inside of the inner electrode 114 electrode (FIG. 9B), extending from the wall of the electrode in inverse direction to the appendages of the shaft.

Shaft Connection

In the first embodiment, one segment shown in FIG. 2B is operated. In further embodiments, two or more segments may be connected in series. Then, two inner electrodes, for example the electrodes 114 (FIG. 5A) or the coiled electrodes in FIG. 9A are mechanically connected via their shafts 108. FIG. 10A shows a shaft joint 143 which is made of electrically insulating material or coated with insulating material such as plastic, Teflon®, wood based materials, and so forth. In alternative embodiments, the shaft joint may electrically conductive by using metals such as steel, titanium, gold, platinum, or carbon, conductive polymers, and so forth. In further embodiments, the joint may be omitted altogether with a shaft extending into the next module or when the next module lacks a shaft. A rounded or concave slope 144 leads to a center pocket 145 of the joint. The pocket has the shape and size matching the end of the shaft 108 that is inserted, as shown in FIG. 10A and FIG. 10B. In other embodiments, there may be no concave slope but one or more planar slopes. In further embodiments there may be no slope at all. The bottom of the pocket is closed. In other embodiments, the center pocket has a through hole. The flip side of the joint has a pocket and a slope as as well, essentially mirroring the front side of the joint. In alternative embodiments, the flip side may be of different shape or size, or the flip side may be blunt.

Holder

In the first embodiment, the inner electrode 114 is held inside the outer electrode 101 by a holder 118, as shown in FIG. 2A and FIG. 2B. The side arms 130 of the holder in FIG. 6A determine the distance between the inner and the outer electrode. The distance between the two electrodes ranges from 0.1 cm to 10 cm. In other embodiments, the distance may be larger or smaller. In the first embodiment the holder has five sidearms 130 each of which has the same length, as shown in FIG. 6A. In further embodiments, the holder may have less than five sidearms or more. In alternative embodiments, the sidearms may have different lengths. Additionally, different shapes than the one depicted in FIG. 6A are possible. In other embodiments, for example, sidearms may be T-shaped. In yet other embodiments, there is only one sidearm, stretching around at least half of the holders circumference. In this case, there is only one sidearm opening 132. In further embodiments, there are no sidearm openings and no sidearms, and the holder is only a disc with a central opening for the inner electrode.

In one embodiment, the holder 118 in FIG. 2A along with the electrode 114 may be inserted by means of a thread as shown in FIG. 3B and FIG. 3C. The threads may be made into the sidearms of the holder and into the inside of the outer electrode 101 in such a way that the bottom of either ridge leaves an unused space or gap 121 or 122. The gap is at least 1 µm deep. In further embodiments, both sides of the thread have such a gap. While in one embodiment the gap may be rounded, it may be not rounded in other embodiments.

In the first embodiment, the outer electrode 101 is made of steel with shutter blades 117 as shown in FIG. 3A. They match the sidearm openings 132 (FIG. 6A) of the holder 118 (FIG. 2A). In alternative embodiments, smaller shutter blades or no shutter blades at all are attached to the outer electrode. In other embodiments, the shutter blades can be soldered, or glued onto the outer electrode. Other methods of attachment are possible as well, such as latching or inserting a ring of shutter blades into an outer electrode groove. The shutter blades may be part of the outer electrode, for example if it is casted or printed.

Inner Electrode Shutter

In the first embodiment, the inner electrode 114 has holes 129 (FIG. 5A) for passing the electrolyte 113 (FIG. 1) through the electrode. In an alternative embodiment, electrolyte flow through the inner electrode can be regulated using shutter blades or internal shutters 139 as shown in FIG. 5B. Internal shutters are attached to either or both distal ends of the inner electrode. The internal shutters match sidearm opening 140 between internal sidearms 141 made into a modified version of the electrode holder 118, as illustrated in FIG. 6C. The inner shutters 139 in FIG. 5B attached to the inner electrode 114 henceforth called inner shutter disc. In the center of the shutter disc, the sidearm openings are attached to a central ring enclosing a central through hole 142. The diameter of the through hole is chosen so that the shaft 108 (FIG. 5A) or the shaft joint 143 (FIG. 10A) can be placed inside. Depending on the size of the entire BES, this central hole can have a diameter of 1-10 cm but may also be smaller or larger. Both, the inner shutter disc 139 in FIG. 5B and the modified holder in FIG. 6C may be made of the same or different materials. However, these materials or their combination must not allow electrical contact between the inner 114 and the outer electrode 101 illustrated in FIG. 1. For example, the inner shutter disc may be made of titanium, steel, platinum, carbon, Teflon®, plastic, wood, glass, and many more but only in case of non-conductive material, the holder 118 (FIG. 2A) must be made of the same non-conductive material.

Operation of Additional Embodiments

Possible Use Cases

In the first embodiment, the BES is operated to produce a methane gas mixture 104 (FIG. 1) from wastewater as source of electrons, hydrogen, and carbon. The bio-electrochemical reactions 103 and 106 in FIG. 1 are involved in the production of the methane mix. Simultaneously, harmful wastewater organics (chemical oxygen demand or COD) are oxidized to $CO_2$. Both, either harmful or useful compounds are contained in the electrolyte 113 shown in FIG. 1. In further embodiments, other hydrocarbons are produced using wastewater or other electron donors. Examples for hydrocarbons are hydrocarbons which can be found in petroleum, for example ethane, ethene, octane, benzene, and so forth. In yet further embodiments, other useful organic compounds can be produced. Examples for useful organic compounds are organic acids such as acetic acid or benzoic acid, alcohols such as ethanol or phenol, ketones or aldehydes, such as acetone or acetaldehyde, syngas (a mix of carbon monoxide and hydrogen gas), and so forth. In alternative embodiments, the BES can be used for removal of other harmful compounds such as nitrogen compounds (e.g. nitrite), sulfides (e.g. hydrogen sulfide), halogenated organic compounds (e.g. vinyl chloride or bromobenzene), metals (e.g. uranium, chromium, or mercury), or other compounds that are involved in bio-electrical redox reactions.

In yet further embodiments, the BES can be used for electrosynthetic reduction reactions 106 (FIG. 1) using $CO_2$ as oxidant, for example, $CO_2$ can be converted to an organic acid such as acetic acid. Other embodiments involve oxidants other than $CO_2$, for example, oxygen ($O_2$), peroxides, protons, sulfur compounds (e.g. sulfate, or sulfite), nitrogen compound (e.g. nitrate or nitrite), organic acids (e.g. acetic acid or benzoic acid), aldehydes (e.g. acetaldehyde or benzaldehyde), ketones (e.g. acetone or benzophenone), alcohols (e.g. ethanol or phenol), halogenated organic compounds (e.g. vinyl chloride or bromobenzene), oxidized metals (e.g. Mn[IV] or U[VI]), and so forth. For example, an alcohol can be made from an acid, for example ethanol from acetic acid or butanol from butyric acid. An alcohol can also be made from an aldehyde or ketone, for example ethanol from acetaldehyde:

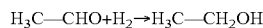

It is also possible to make a hydrocarbon from an alcohol, for example ethane or ethene from ethanol, or benzene from phenol. Further precursors for hydrocarbons are acids or aldehydes. In alternative embodiments, other reduced products can be made, for example from the aforementioned oxidants alone or combinations thereof.

While some reactions, such as $O_2$ or peroxide reduction can be carried out using non-biological catalysts, others can proceed via biological catalysts such as microorganisms. Examples for microorganisms carrying out some of the aforementioned reactions are *Dehalococcoides, Sulfurospirillum*, for dehalogenation, *Desulfovibrio, Desulfococcus*, for sulfate reduction or hydrogen production, *Geobacter* and *Shewanella* for Mn(IV) or U(VI) reduction, *Pseudomonas* for nitrate reduction, *Kuenenia* for nitrate reduction, *Saccharomyces* for aldehyde reduction, *Clostridium* for ketone reduction, *Methanosarcina* for ethanol reduction, and so forth.

Yet more examples for microorganisms carrying out these reactions are *Propionibacterium, Sporomusa, Moorella, Lactobacillus, Leuconostoc, Pediococcus, Lactococcus, Streptococcus*, or *Clostridium* for producing organic acids such as acetate, propionate, butyrate, lactic acid, pyruvate, 2-oxobutyrate, benzoate, and so forth. Species belonging to these genera may also produce alcohols such as ethanol, propanol, 2-propanol, butanol, hexanol, as well as ketones like acetone, and so forth. Other examples for microorganisms catalyzing redox reactions on aldehydes, ketones, or alcohols are species belonging to the genera *Bacillus, Saccharomyces*, or *Candida*. Typical examples for microorganisms producing hydrocarbons are methanogens such as species belonging to the genera *Methanobacterium, Methanothermobacter, Methanobrevibacter, Methanosaeta, Methanococcus, Methanocalculus, Methanoculleus, Methanocorpusculum, Methanosarcina*, and many more. Other microorganisms producing hydrocarbons are, for example, prokaryotic algae such as Synechococcus or *Synechocystis*.

In the first embodiment, the reaction 103 and 106 in FIG. 1 are biological reactions carried out by microorganisms. In other embodiments, these reactions can be a combination of biological and non-biological reactions. In further embodiments, such reactions can also be catalyzed by biological compounds produced by biological cells. Examples for biological compounds are proteins (e.g. hydrogenases or oxidases), catalytic centers of proteins (e.g. hydrogenases or lipases), or porphyrins (e.g. vitamin $B_{12}$ or chlorophyll), peptides, lipids, alcohols, nucleic acids, bio-polymers, and so forth. Biological cells or compounds can be prepared inside or outside the BES. Combinations of different biological and/or non-biological material are possible as well. For example, the outer electrode 101 in FIG. 3, catalyzes non-biological electrochemical reactions. For this purpose, the outer electrode may bear non-biological material, for example platinum, platinum on carbon, mixed metal oxides, sulfides, or any other catalyst facilitating the desired reactions.

In the first embodiment, hydrogen gas is the intermediate for methane gas production. Many of the aforementioned redox reactions in further embodiments involve hydrogen gas ($H_2$) as intermediate electron carrier. In other embodiments, other redox carriers can be involved, for example nicotineamide-adenine dinucleotides (NAD), flavins (FMN), dyes (e.g. neutral red, resazurin), quinones (e.g. hydroquinone, anthraquinone 2,6-disulfonic acid [AQDS]), formic acid, cobalt sepulchrate, benzyl viologen, methyl viologen, and so forth.

General Operation

In the first embodiment, the outer electrode 101 of the BES is also its tubular housing without additional layers as shown in FIG. 1 and FIG. 2A. In some of the further embodiments, an additional layer of electrical insulation is used. In yet further embodiments, the tubular shape allows easy wrapping of the outer electrode by one or more heating devices, for example pipes, ducts, or tubings that carry a heating fluid or steam. The heating device may also be a heating mantle, tape, or wire. Heating the outer electrode and its interior allows pasteurization or sterilization. In other embodiments, the BES can be cooled by surrounding it with a cooling device such as pipes, ducts, or tubings that carry a cooling liquid like water or other cooling liquids. The application of such temperating devices can be accomplished without opening the BES.

In the first embodiment, the BES is operated as an electrolysis cell treating the wastewater electrolyte 113 and producing the methane gas mix 104 as shown in FIG. 1. In another embodiment the BES is operated as fuel cell for the purpose of producing electrical power with an electrical load 146 in FIG. 1. Like the DC power supply, the load electrically connects the outer electrode 101 and the inner electrode 114. Such an electrical load can be one or more useful electronic modules which convert electric energy, for example into kinetic energy such as in electric motors. Since the number of possible useful electronic modules is so large, further examples are omitted here. When operated as fuel cell, the outer and the inner electrodes simply provide the electrochemical potential required to be operated as fuel cell. Then, these electrochemical potentials are determined by the redox reactions 103 and 106 in FIG. 1 as opposed to a DC power supply.

In the first embodiment of the BES in FIG. 2A, the outer electrode 101 is the cathode and the inner electrode 114 is the anode which is also illustrated in the schematic FIG. 1. In alternative embodiments, anodes and cathodes are switched such that the outer electrode 101 is the anode and the inner electrode 114 the cathode. This is useful when the BES is operated in fuel cell mode. Then, it may be desirable to switch anode and cathode so that the inner electrode is operated as cathode with air moving through the electrode. One or more electrodes can be operated to produce the aforementioned useful compounds and/or to remove harmful compounds.

Gas Outlets/Float Switches

In the first embodiment, the gas outlet 105 in FIG. 1 is the float switch as shown in FIG. 4A and regulates the extraction of the methane gas mix 104 (FIG. 1). When the level of liquid inside the BES reaches the point where the floater 124 (FIG. 4A) touches the wall of the float switch 126 (FIG. 4B), the gas outlet 105 (FIG. 1) is closed. Opening or closure of the float switch controls a pressure-regulated valve which is connected further downstream the gas collection system of the BES. In an alternative embodiment, the conductivity sensor shown in FIG. 8A and FIG. 8B is used to sense the level of liquid. The sensor senses the high electric conductivity of the electrolyte compared with the low electric conductivity of the gas inside the gas outlet 105 (FIG. 1). The electric conductivity sensor also regulates a downstream gas valve such that it opens when a certain resistivity is surpassed. The resistivity can be set by the user or by an algorithm.

Some embodiments provide a BES that can be operated on unstable ground. Examples for unstable ground situations are vehicles, ships, aircrafts, or spacecrafts. Under gravity, the difference in density permits the use of a float switch as depicted in FIG. 4A. When the conductive surrounding of the floater 128 (FIG. 4C and FIG. 4D) is in contact with the wall 126 (FIG. 4B), a valve is switched to interrupt gas extraction from the BES. Different coverage of the conductive surrounding 128 (FIG. 4C and FIG. 4D) confers different sensitivity to the float switch. For example, a fully covered floater is very sensitive because the probability of electrical contact is very high, which is shown in FIG. 4C. A high sensitivity float switch keeps the gas outlet mostly closed. Less conductive coverage, as shown in FIG. 4D, results in lower sensitivity. The design of the float switch is such that it can be operated on unstable ground under gravity. The angle and number of the gas outlets 105 in FIG. 2A and FIG. 2B are chosen based typical tilts of the moving vessel or vehicle. Typically, gas outlets are spaced tangentially between 5°-45° and longitudinally between ⅓-1/10 of the length of the outer electrode 101 as shown in FIG. 2A.

In the first embodiment, the BES is operated under terrestrial gravity. In alternative embodiments, the BES is operated under zero or near-zero gravity. Then, gas extraction is accomplished by using the embodied conductivity sensor, frits, gauze, membranes, or other porous separators that retain liquid but allow passage of gas. When operated under zero gravity, the gas outlets may be placed all over the outer electrode as the probability of exposure to gas bubbles is the same everywhere.

Inner Electrode Configurations

In the first embodiment, the inner electrode 114 (FIG. 5A) has a porous wall which confers mechanical stability and retains the filling material inside the electrode. For the purpose of filling retention, the inner electrode may have an extra layer of porous material with smaller pore sizes than the pores 129 in FIG. 5A. Larger pores and thicker walls confer mechanical stability while the filling material is retained by one or more layers of mesh or cloth. In alternative embodiments, for example when the BES is bent or used in a bent, it may be desired that the inner electrode is elastic. Then, the inner electrode may be only cloth or mesh with or without filling material. Cloth or mesh without filling material may be a coil 137 around the inner shaft 108 as illustrated in FIG. 9A.

Both, the filling material and the housing of the inner electrode 114 in FIG. 5A may catalyze electrochemical the reactions 103 or 106 (FIG. 1). They can be coated with the aforementioned biological catalyst or with a non-biological catalyst. In other embodiments, the filling is electrically connected to the shaft by appendages 138 such as wires, filaments, or fibers that may form a brush together with the shaft as shown in FIG. 9B. In some embodiments, the appendages provide better electrical connection with the shaft 108 of the hollow electrode 114 shown in FIG. 5B and the filling. In other embodiments, such a brush is the inner electrode 114 (FIG. 1) itself without an additional housing. In further embodiments, the appendages 138 and the shaft 108 in FIG. 9B are hollow and are capillaries. The electrolyte 113 (FIG. 1) can be injected or extracted via these capillaries.

In the first embodiment, the wastewater electrolyte 113 carries the substrates for the redox reactions 103 and 106 in FIG. 1. In other embodiments, the electrolyte is not be laden with substrates involved in the chemical reactions 103 and 106 in FIG. 1. Then, substrates are injected sequentially when the electrolyte is already present, for example the substrate is added as a concentrate. In some embodiments, the appendages 138 in FIG. 9B are capillaries used for substrate injection. For example, gases can be injected or extracted using these capillaries. In other embodiments, the injected gas may be steam which allows pasteurizing or sterilizing the inner electrode 114 in FIG. 5A along with the interior of the BES. Similarly, the appendages 138 in FIG. 9B are capillaries and are used to extract the product while retaining the electrolyte inside the BES, for example when the product is the methane gas mixture 104 of the first embodiment in FIG. 1. In other embodiments, the appendages 138 in FIG. 9B are capillaries which are filled with porous material to prevent back flux of the electrolyte when extracting the product. In further embodiments, the porous material may be membranous to separate the product from the electrolyte.

In the first embodiment, the filling of the inner electrode 114 in FIG. 5A is electrically connected to the wall of the inner electrode. In further embodiments, the fibers extending from the wall into the interior of the inner electrode are similar to those of the fibers 138 of the shaft 108 in FIG. 9B. They serve the same operational purposes as the shaft fibers such as better electrical contact with the filling, infusion, or extraction of electrolyte as well as substrates or products. Gases may be injected in the form of steam, for example to allow pasteurization or sterilization of the inner electrode and the entire BES.

Power Supply

The first embodied BES shown in FIG. 1, is operated as electrolysis cell connected to a DC power supply 110 which converts AC to DC voltage. AC power is provided by a gas turbine which uses the methane gas mixture 104 produced by the BES. In further embodiments, AC power can be generated by turbines converting energy from wind, water, or steam into electrical power. In yet further embodiments, the DC power supply uses DC power as input. Examples for DC power input are solar cells or batteries. In some embodiments, the DC power source may provide the required voltage directly and a transforming DC power supply is not required. Examples for a DC power source which does not require a DC power supply are solar cells, batteries, or fuel cells. Multiple the DC power sources may be connected to the BES in series or in parallel.

In the first embodiment, the DC power supply 110 in FIG. 1 is controlled by an algorithm that maintains a constant potential between the inner electrode 114 and the reference electrode 112. In alternative embodiments, the potential between the reference electrode 112 and the outer electrode 101 can be controlled. An offset potential $E_{off}$ set by the user helps to adjust the potential in case noise interferes. In an alternative embodiment, $E_{off}$ can be set according the specifications of the DC power supply 110 or the voltmeters 109 and 111, or by an algorithm which determines the optimal offset potential. For example, the optimal offset potential can be determined during operation of the BES by recording failures to set the correct potential or in case of oscillating output potentials $E_n$.

Shaft

In the first embodiment, the shaft 108 in FIG. 5A allows rotation of the inner electrode 114 around the central longitudinal axis 119 (FIG. 2A). Rotation allows flow control together with the provided shutter blades 117 and the sidearms of the holder 118 in FIG. 4. In further embodiments, there are no shutter blades, for example when no flow control is desired between the inner and outer electrodes. In yet further embodiments, the number of shutter blades and sidearm openings allows the electrolyte flow to become more or less turbulent between the inner and outer electrode. In other embodiments, rotation of the inner electrode 114 serves the purpose of better mixing of the electrolyte 113 in FIG. 1. Better mixing helps to the expel gaseous 104 from the electrolyte 113 so they can be collected using the gas outlets 105. In other embodiments, mixing also helps ionic diffusion, as well as dispersion of biological material, or products and substrates of the electrochemical reactions 103 and 106 in FIG. 1. The hollow embodiments of the shaft 117 and the hollow appendages 138 in FIG. 9B can be used for seeding the BES using a suspension of biological cells or enzymes pumped or sucked through the shaft and capillaries. Seeding this way allows for better dispersion of biological catalysts throughout the inner electrode 118 and the entires BES shown in FIG. 2A.

Holder

In the first embodiment, the inner electrode 114 of the BES is held inside the outer electrode 101 by the two holders 118 as shown in FIG. 2A and FIG. 2B. In FIG. 6A, the electrode holder has a central hole 131 for insertion of the inner electrode 114 as shown in FIG. 2A. Central placement of the inner electrode allows evenly distributed redox gradients. In further embodiments, the central hole of the inner electrode is off-centered, which allows off-centered rotation of the inner electrode. This required if varying electrochemical redox gradients are desired between the outer 101 and the inner 114 electrodes, for example when more than one substrate is involved in the reactions 103 or 106 in FIG. 1. In other embodiments, the distance between the inner and the outer electrode is in optimal balance to minimize the inner resistance of the electrolyte and to reduce undesired substrate and product crossover between the inner and the outer electrode. The distance between the two electrodes is chosen by the user of the BES. A typical criterion for choosing the distance is the electrolytic resistance between the inner and the outer electrodes. The distance is depending on the acceptable tolerance for the electrolytic resistance between the two electrodes, or other criteria.

Seeding

In the first embodiment, turning the inner electrode 114 along with its holder 118 around the axis 119, as shown in FIG. 2A, allows volumetric flow control of the electrolyte in horizontal direction. In another embodiment, the thread of the outer electrode 101 matched by the thread of the sidearms 130 (FIG. 6A and FIG. 6B) of the holder 118 to disperse catalytic material on the outer electrode, as shown in FIG. 3B and FIG. 3C. The threads on the outer electrode and the holders also allow insertion of the inner electrode 114 in longitudinal direction by rotation around the axis 119, as shown in FIG. 2A. Catalytic material can be applied onto the thread of the holder and/or the the thread of the outer electrode. Rotation and insertion of the inner electrode then disperses the catalytic material on the surface of the outer electrode 101 as the inner electrode 114 is inserted. In other embodiments, the biological material is not not dispersed by screwing the holder 118 into the outer electrode 101, as shown in FIG. 1A, but by spraying the material onto the outer electrode or the holder, or both. Subsequent screwing of the holder into the outer electrode further helps dispersing the biological material.

In some embodiments, this catalytic material comprises biological cells. These cells are suspended in a mixture of high viscosity which also has a low surface tension on the outer electrode 101 in FIG. 3A, so that the cell suspension or other catalytic material better adheres to the electrode surface. Examples for highly viscous matrices are glycerol, mineral oil, polymers, and so forth. In other embodiments, the suspended catalytic material is non-biological. In further embodiments, the viscous matrix hardens after application and the catalyst then adheres to the electrode surface within the hardened matrix. Such matrices are resins, or polymers such as agarose, acrylamide, Nafion, dextran, carrageenan, alginic acid, polyvinyl alcohol, polyhydroxy alkanoates, and so forth. To disperse the catalytic mixture, the inner electrode 114 is screwed into the outer electrode using the threads on both, the holder 118 and the outer electrode 101, as described above. After complete insertion of the inner electrode, the first holder is removed and the inner electrode is held in place by at least one second holder. The threads of the second holders allow gaps 121 and 122 between the holders and the outer electrode, as shown in FIG. 3B and FIG. 3C. The catalytic material remains on the surface of the outer electrode 101 (FIG. 3A) when the inner electrode 114 (FIG. 2A) is removed, for example during maintenance. The gaps may be either on the arms of the holders 121 (FIG. 3B), or the outer electrode 122 (FIG. 3C), or both.

In the first embodied BES, biological cells are sessile. In other embodiments, no sessile biological cells are used to catalyze the 103 or 106 as shown in FIG. 1. Then, biological cells as well as biological non-cellular catalysts, or non-biological catalysts are suspended or dissolved in the electrolyte 113 in FIG. 1. Suspended biological cells may be planktotic. That is, biological or non-biological catalysts never form aggregates. In such cases, the electrolyte 113 is pumped or sucked into the BES using pumps connected to the BES via adapters using the provided flange 116 in FIG. 2A. In other embodiments, non-sessile or planktotic cells may be pumped or sucked into the BES using the hollow embodiment of the shaft 108 and the hollow appendages or capillaries 138, as depicted in FIG. 9B. Suspended biological cells may then be retained inside the BES using the embodied shutter mechanisms 139 (FIG. 5B) for the inner electrode 114 (FIG. 5B) along with shutter blades 141 of the modified holder 118 shown in FIG. 6B and FIG. 6C. Likewise, the embodied shutter mechanism for the outer electrode 101, comprises outer shutter blades 117 and electrode holder sidearms 130 (FIG. 6A and FIG. 6B), as shown in FIG. 2A. The outer electrode 101 shutter mechanism (FIG. 2A) then helps to retain biological cells suspended in the electrolyte 113 (FIG. 1) of this electrode.

Modularity

In the first embodiment, the assembled BES shown in FIG. 2B is one module which can be operated as stand-alone or as part of a cluster together with other modules that are identical, as shown in FIG. 12A, or are modified in alternative embodiments. For better illustration, FIG. 12A shows four fully assembled modules connected in a serial configuration 145, followed by one module 146 without the outer electrode 101 (FIG. 2A), and one more module without any parts 147 except two holders 118 (FIG. 2A). In one embodiment, such clusters of BES modules can be operated in series where the effluent of one module is the influent of a subsequent module. Serial clusters of the BES can be connected directly to each other (shown in FIG. 12A), for example by using the provided flange 116 shown in FIG. 2A. Gaskets 115 between two flanges, shown in FIG. 2A, FIG. 2B, and FIG. 7A, electrically insulate the modules and can be made of Teflon®, rubber, fabric, wood-based materials, and so forth. In alternative embodiments, the connection between the modules shown in FIG. 2B is made by inserting a pipe, tubing, angle, or similar connecting elements. In further embodiments, identical or modified BES modules can be operated in parallel. In yet further embodiments, identical or modified BES modules can be operated in series and in parallel. In an alternative embodiment, the BES module is operated in batch mode, i.e. the electrolyte is loaded into the module and not moved until removed again. The electrolyte may be mixed or stirred in either flow-through or in batch mode.

When the embodied BES modules are operated in series, the shafts of two inner electrodes 114 (FIG. 5A) may be connected using a joint 143 as shown in FIG. 10B. The joint mechanically connects two shafts at their ends while electrically insulating them. This operation allows separate electric control of two of the inner electrodes 114 (FIG. 5A) while simultaneously rotating them together. For this purpose, the joint is electrically insulating but has two geometrically mirrored sides, or sides that mechanically accept shafts of different shapes. In alternative embodiments, the inverse is desired and another joint electrically connects two inner electrodes while there is no mechanical connection. In this case the joint may have a blunt flip side and is in contact with another blunt side of a second joint so they can freely rotate against each other. Then, both joints are in electrical contact, for example by using the blunt end or by using carbon brushes attached to these blunt ends. In further embodiments, different combinations of shaft joints with respect to their geometries and materials are possible depending the specific application. There may also be no joints at all or one shaft of one electrode reaches into the other electrode when both, mechanical and electrical contact are desired.

In the embodied shaft joint 143 shown in FIG. 10A, the concave slope 144 leads into the center pocket 145. This slope allows easy positioning during assembly and disassembly of two of the inner electrodes 114 (FIG. 5A) along with their shafts 108 (FIG. 5A), which is depicted in FIG. 10B. As shown in FIG. 10A and FIG. 10B, the pocket 145 at the end of the slope 144 fixes the shaft 108 in its final position 815 and has therefore a shape that matches the cross section of the shaft 108. If different shaft geometries are used on either side of the joint, the pockets are also different, matching the shaft geometries. The end of the shaft 108 in FIG. 10B itself may be convex or rounded as well to further facilitate assembly. The bottom of the pocket 145 is closed but may have a through hole in case electrolytic or gas connection between two hollow shafts is desired.

Figure 11:
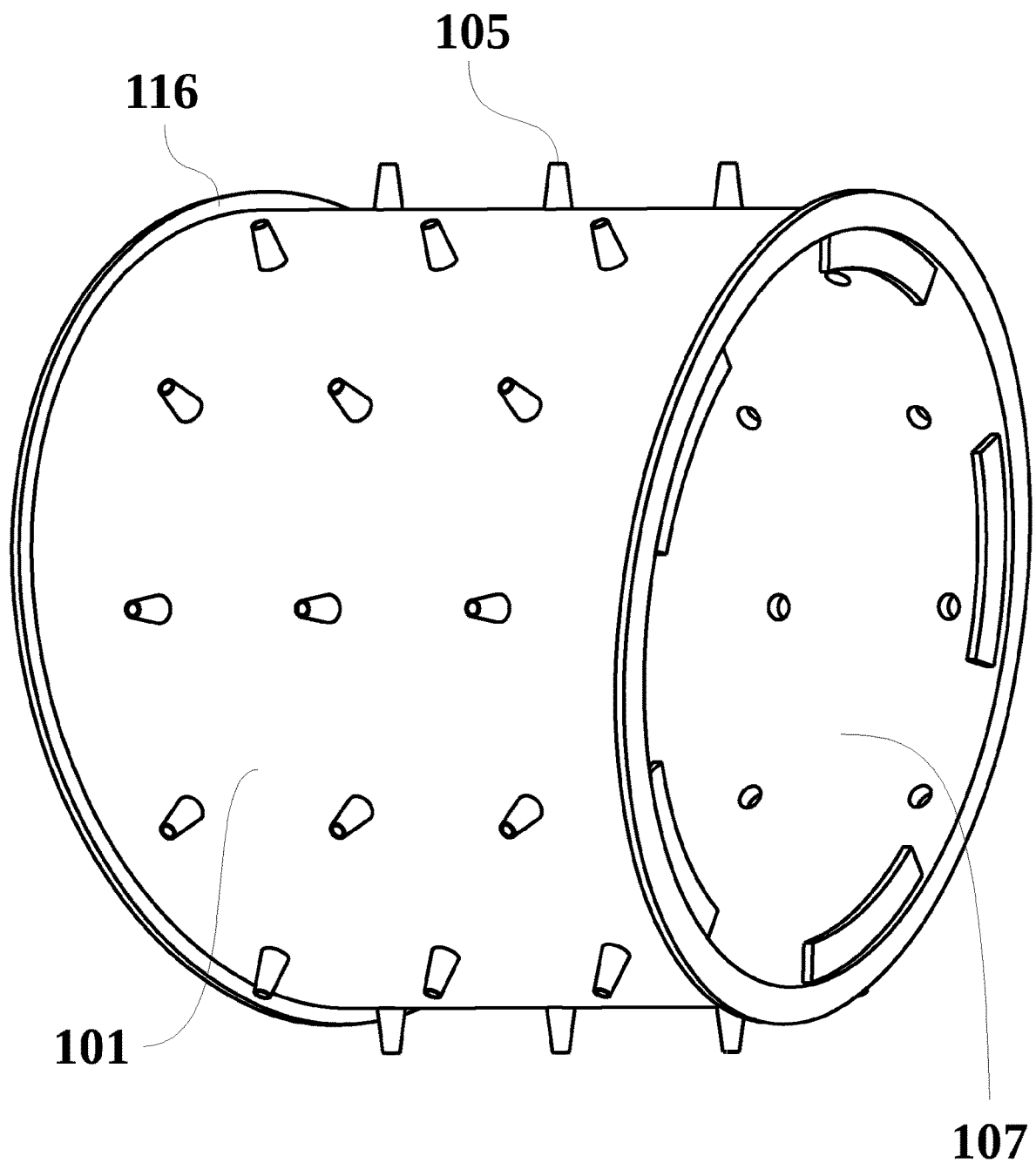
FIG. 11 Outer electrode with slanted ends.

In further embodiments, the BES modules connected to each other in series are operated under low gravity or when space is a limiting factor. Then, the BES modules of a fully assembled system are connected using slanted housing electrodes 101 (FIG. 11), or bent or slanted inserts to form a ring as shown in FIG. 12B. Under low gravity, such a ring can be rotated to force gas accumulation near the inner ring hole by generating centrifugal force. In other low gravity embodiments, the ring BES is not rotated and gas is collected based on probability all over the reactor. The gas outlets 105 may then be placed all over the outer electrode 101 as shown in FIG. 12B. In further low gravity embodiments, gases are collected inside the reactor using the appendages 138 in FIG. 9B which are hollow as well as the shaft 108.

Advantages

As outlined in the detailed description of the invented BES, some embodiments have the following advantages. Many of the advantages emerge from the tubular shape of the BES where the housing and the outer electrode are identical, for example:

a) This design allows the easy double use of the outer electrode for housing the reactor which saves material and weight, making it available for mobile applications where space and weight are critical factors.

b) The tubular design allows operation under high pressure.

c) The horizontal application makes collection of gases easier when the BES is operated on unstable ground, making it available for mobile applications, for example on vehicles or ships. For this purpose, controllable gas outlets are provided which can collect gases at different tilts.

d) The tubular outer electrode housing allows easy heating or cooling of the electrode and the entire BES. Thus, the outer electrode and the BES interior can be sterilized. With the housing being identical with the outer electrode, heat loss is minimized when the BES are temperated.

e) The tubular design where the outer electrode is also the housing offers easier integration into existing piping systems with easier maintenance. This design and the ensuing segmentation allows more efficient serialization and parallelization of the BES which is important for scalability.

f) Serialization permits cascaded reactions where the product of one step is the substrate of a subsequent step.

g) The serialized tubular design offers operation under zero gravity, for example when BES segments are arranged in the form of a ring or gas outlets are placed all around the outer electrode tube.

h) The parallelized operations allow higher flexibility when the influx volume varies.

i) The tubular design adds a third dimension to the inserted inner electrodes, thereby greatly improving surface-to-volume ratios and reaction kinetics. For example, a brush or drum filled with catalytic granules can be placed inside.

j) Insertion of a tubular inner electrode matching the tubular outer electrode enables an evenly distributed redox gradient between the two electrodes. The inner electrode is held in place by holders which maintain a constant distance between the electrode throughout the BES, which stabilizes the redox gradient. Reactions inside can therefore be more efficient and stable.

k) When different redox gradients are desired, the provided holders can easily be modified to have off-centered insertion holes or different arm lengths so that rotation of the inner electrode against the outer electrode distributes the differences internal redox gradients.

l) The inner electrode drum is sturdier than previous designs because it can have multiple wall layers, for example, the outer wall of the drum can be made of sturdy titanium for mechanical robustness and an extra membrane can be easily wrapped around the outside of the drum to prevent crossover of compounds.

m) The tubular reactor design also solves the problem of dead space where gas bubbles become entrapped by eliminating all edges. Now, gas accumulations can easily be extracted on the top of the horizontal outer electrode.

n) The tubular BES design uses space more efficiently because electrodes can be fully submerged in the electrolyte and no dead zones occur inside the reactor.

o) The tubular BES design uses a facile opening and closing mechanisms which can be individually controlled for each serial or parallel segment.

p) The flow of the electrolyte can also be controlled for each individual electrode. Such flow control can be necessary, for example when steady state conditions are required. Then, the BES will be operated in flow-through mode. Flow control of the electrolyte is also necessary to adjust redox potential to the range limits of the desired reaction (e.g. in fuel cell mode) or the connected power supplies (e.g. in electrolysis mode).

q) In other situations, the BES can be operated in batch mode which may be desired for slower reactions or when the volume of the reaction mixture is smaller. This can make reactor operation more economical in such situations.

While the provided BES are of tubular shape, allowing the insertion of high surface-to-volume inner electrodes such as drums or brushes, such inner electrodes need not to be of the same shape. For example, conical or ellipsoid shapes, or conical shapes with cross-, star-, or egg-shaped cross section geometry allow different redox gradients between the inner and the outer electrode. This is an advantage when, for example, different substrates react at specific redox potentials.

The inner electrode drum can be filled with catalytic material and operated as anode or cathode. Filling the inner electrode makes the BES easy to use and very versatile as it allows an enormous variety of fillings. One aspect is, for example, to possibility to seed the inner electrode with pre-acclimated material. A typical application of the BES is wastewater treatment. Wastewater is often laden with nutrients. Energy from such nutrients is extracted to produce methane gas mixtures. Multiple existing ways of storing or transporting it are available, making the BES useful in a wide variety of situations, for example for grid injection, transportation, and so forth.

The scalability of the BES allows its application for example in bio-remediation. In one example, the inner electrode can be filled with radioactively contaminated soil. Insoluble U(IV) oxide can be oxidized by microorganisms to better soluble U(VI) oxide and washed out of the soil to be further processed. Further processing can involve a subsequent BES where U(VI) oxide is re-reduced inside another internal drum of another segment containing a solid absorbent. The flow can easily be redirected using the provided shutter mechanisms. This and other examples given in the description further illustrate the versatility of the operation of the provided BES.

The internal electrode can be rotated using the provided shaft. In some embodiments, more than one shaft can be used. Using more than one shaft is attractive, for example, when the BES are very large. For very large BES, using more than one shafts permits improved application of rotating forces, thereby lowering material wear to extend the lifetime of the inner shafts. This is attractive for long term applications, for example in wastewater treatment facilities.

Using the shaft for the inner electrode also allows better electrical contact to the electrodes filling which can be even further improved by adding appendages to the shaft so it becomes a brush. Shaft and appendages can be hollow to become capillaries. Through such capillaries, steam can be injected to sterilize the inner electrode or the entire BES. Directly injecting steam into the BES using capillaries reduces heat loss, making the preparation and operation of the reactor more economical. Sterilizing the BES can be necessary, for example, when biological material of high purity is used to catalyze reactions. Examples are specific compounds in the food or pharmaceutical industry such as sugars, amino acids, biopolymers, steroids, and many more. However, as outlined in the description, such capillaries and shaft have more than one use, which further shows how versatile the invented BES are.

The invented BES can easily be serialized. However, they can also be parallelized. Parallel clusters are an advantage, for example for wastewater treatment applications with varying volumes of input water. The facile integration into existing piping structures due to its tubular housing-electrode make parallelization easy because existing flow control systems can be used in addition to the ones provided in the invented BES. This makes controlling the BES even more flexible.

In one embodiment, the BES can be seeded using a thread on the outer electrode and the holder of the inner electrode. Such seeding using pre-acclimated microbial suspensions or pastes reduces startup time. Other catalysts may be applied to the outer electrode surface as well using the same thread, which further emphasizes the versatility of the BES. The thread on the surface of the outer electrode also increases the surface area of the electrode. This has the advantage of offering more catalytically active sites which accelerates reactions on the outer electrode. This is an additional economic advantage of the BES.

Catalytic material, such as biological cells, may be applied being embedded in a matrix of a liquid of high viscosity as described above. Using such a matrix together with the provided threads disperses the catalytic material on the surface of the electrode more evenly. Choosing a matrix that has a low surface tension on the outer electrode improves adherence and reduces the amount of catalyst necessary to start and operate the BES. It is clear that this is a great economic benefit.

The BES can be operated as electrolysis cells or as fuel cells. If they are operated as electrolysis cells, their modular design allows using segments that are within range of power supplies that handle lower currents than the entire reactor would. This is important because many bio-electrical applications use low voltages as high currents. It makes the operation of the reactor more economical. Using individual power supplies to power each segment also facilitates cascaded reactions where the redox potential of a preceding reaction may be different from that of a subsequent reaction.

Using power supplies that are software controlled by the provided algorithm allows operation with off-the-shelf components. Such components or usually inexpensive because they are produced in high quantities, making the operation of the BES even more economical and flexible. The provided algorithm is simple to program. In some embodiments, it uses an offset potential to calculate the next cell potential. This offset potential is useful when noise interferes with low potentials and allows better control and higher stability of the applied redox potential.

CONCLUSIONS, RAMIFICATIONS, AND SCOPE

Thus the reader will see that at least one embodiment of the BES provides a more versatile and economical system.

As described above, the BES can be used for wastewater applications, electrosynthesis, or decontamination. They uses inexpensive materials, such as standard steel pipes as outer electrodes and housings, granular filling materials for inner electrodes, and off-the-shelf power supplies, allowing full scalability. Their tubular design, where the housing is the outer electrode, makes efficient use of resources such as space, weight, and time. The BES also allow full scalability and operation on unstable ground or at zero or low gravity. Both electrodes can be seeded using simple procedures which is facilitated by design features such as threads on the outer electrode or the possibility to fill the inner electrode using pre-acclimated material. In combination, all of the described embodiments provide versatile, inexpensive, and efficient utilities for a wide range of bio-electrical applications.

While my above description contains many specificities, these should not be construed as limitations on the scope, but rather as an exemplification of several embodiments thereof. Many other variations are possible. For example, the BES may be used for energy storage applications, sometimes also called power-to-gas. In such scenarios, the BES use excess electrical power, for example from renewable power sources. The outer electrodes of the BES can produce hydrogen, methane, or liquid hydrocarbons while the internal electrodes may carry a water-splitting catalyst producing oxygen. Then, the produced hydrogen, methane, or higher hydrocarbons can be stored elsewhere for later use, for example when less renewable power is available.

In further embodiments, the tubular shape may also be modified. For example, a cross section of the outer electrode may be ellipsoid, drop shaped, rectangular, hexagonal, octagonal, cross-shaped, or star-shaped. This can be useful, for example, when the space in which the BES is operated requires such a change. The inner electrode may or may not match the shape of the outer electrode. In yet further embodiments, the shape of the outer electrode may be spherical or approximately spherical (e.g. egg-shaped) with an inner electrode of identical or similar shape. This can be useful in batch operations, for example as enhanced anaerobic digester. Under zero-gravity, a spherical shape may also be desired instead of the embodied ring shape.

In some embodiments, the tubular outer electrode is matched by a tubular inner electrode. In other situations, multiple inner electrodes may be used. This can be the case, for example, when they are filled with different catalysts to carry out cascaded reactions inside the inner electrode when it is not important what the outer electrode does. The inverse is possible as well. Multiple outer electrode can be connected and one inner electrode can be inserted.

The various embodiments of the provided BES are dimensioned to allow operation inside existing or newly constructed rooms, buildings, or plants of various sizes. However, the BES may also be operated out-doors, for example on farmland or in short term applications when the construction of buildings is not desired. In other embodiments, the BES may be fully or partially submerged in a liquid, for example wastewater, or contaminated water in the environment. Moreover, the BES may also be operated underground, for example in mines, caves, boreholes, and so forth. In further embodiments, the BES may be miniaturized to millimeter or micrometer scale. Applications for miniaturized BES can be sensors or highly clustered operations. Due to the scalability of the provided BES modularization may also be accomplished by inserting smaller variations of the BES into a larger version. Many such insertions are possible.

Accordingly, the scope should be determined not by the embodiments illustrated, but by the appended claims and their legal equivalents.

I claim:

1. A control method for electrochemical systems for controlling a setpoint potential between one or more first and second electrodes of an electrochemical cell, comprising:
    a. measuring the electrical potential between said first and second electrodes at a time one,
    b. measuring the electrical potential between said first electrode and one or more third electrodes at said time one or close to said time one,
    c. setting a new electrical potential between said first and third electrodes at a time two by multiplying said setpoint potential with the result of the division of said time one potential between said first and third electrodes by said time one potential between said first and second electrodes, and whereby setting said new potential between said first and third electrodes at said time two results in a new potential between said first and second electrodes at a later time that is at least close to said setpoint potential.

2. The control method of claim 1 where an offset is added to any one potential of said control method.

3. The control method of claim 2, further comprising: setting the offset based on user input.

4. The control method of claim 2, further comprising: setting the offset based on a specification of a voltmeter used to measure at least one of the potentials.

5. The control method of claim 2, further comprising: setting the offset based on a specification of a power supply.

6. The control method of claim 2, further comprising: setting the offset to an optimal offset value using an algorithm.

* * * * *